(12) United States Patent
Drongelen

(10) Patent No.: US 6,224,549 B1
(45) Date of Patent: May 1, 2001

(54) MEDICAL SIGNAL MONITORING AND DISPLAY

(75) Inventor: Wim van Drongelen, Madison, WI (US)

(73) Assignee: Nicolet Biomedical, Inc., Madison, WI (US)

( * ) Notice: Subject to any disclaimer, the term of this patent is extended or adjusted under 35 U.S.C. 154(b) by 0 days.

(21) Appl. No.: 09/295,167

(22) Filed: Apr. 20, 1999

(51) Int. Cl.$^7$ ........................................................ A61B 5/00
(52) U.S. Cl. ........................ 600/300; 600/554; 600/558; 600/559
(58) Field of Search .................................... 600/300–301, 600/309, 322, 345, 437, 481, 485, 490, 500, 503–504, 508–509, 526, 529, 549, 561, 587, 554–555, 558–559

(56) References Cited

U.S. PATENT DOCUMENTS 5,724,025 * 3/1998 Tavori .
5,724,032 * 3/1998 Klein et al. .
6,050,940 * 4/2000 Braun et al. .

OTHER PUBLICATIONS

Nicolet Biomedical, "Bravo EEG Acquisition User Guide", Jun., 1998.
Nicolet Biomedical, "Bravo Electromyography and Nerve Conduction Studies Reference Guide", Dec., 1999.
Nicolet Biomedical, "Bravo EP Evoked Potential User Guide", Jun., 1998.

* cited by examiner

Primary Examiner—Cary O'Connor
Assistant Examiner—Ryan Carter
(74) Attorney, Agent, or Firm—Foley & Lardner

(57) ABSTRACT

The present invention provides a medical signal monitoring system and method for displaying physiological signals of different types and modalities in different formats on a single system. Physiological signals, e.g., electrical physiological signals from electrodes attached to a subject, are provided to the system. The raw wide band physiological signals may be recorded on disk, and may be processed multiple times to display desired signals of interest. The parameters used to process the signals to be displayed are selectable by an operator employing a user interface. The user interface allows an operator to define a set of panels in which one or more signals will be displayed. The type of panel selected to display the signal determines the basic format of the signal to be displayed, e.g., various types of waveforms. A signal to be displayed in a panel is defined by selecting, for example, the signals from two electrodes attached to a subject from which a montaged pair signal to be displayed is derived. The modality of the signal to be displayed, e.g., EEG, EMG, or evoked potential (EP) is operator selectable employing the user interface. The user interface also provides for operator selection of other display and analysis parameters, such as triggering, averaging, and spectral trend analysis. A signal to be displayed in a panel may be triggered from an auditory, visual, or electrical stimulation signal provided to a subject. The characteristics of the stimulation to be provided to the subject are operator selectable employing the user interface. A separate stimulus context may be established for each panel defined by an operator. Switching between different stimulus contexts is achieved via the user interface by activating a panel to which a stimulator context has been assigned.

46 Claims, 20 Drawing Sheets

MEDICAL SIGNAL MONITORING AND DISPLAY

FIELD OF THE INVENTION

The present invention pertains generally to medical monitoring equipment, and particularly to methods and devices for analyzing and displaying physiological signals provided by such equipment.

BACKGROUND OF THE INVENTION

Medical monitoring involves monitoring the body of a subject to determine the state of health of the subject and to detect, identify, and diagnosis changes or abnormalities in the state of the body which may be indicative of problems or for treatment evaluation. Medical monitoring may involve, for example, the motion of a subject's body, temperature or chemical changes of the subject's body, and/or audible or electrical signals generated by the subject's body. For example, electroencephalography (EEG) is a form of medical monitoring wherein the electrical potentials of the subject's brain are monitored by attaching electrodes to the subject's scalp. In electromyography (EMG), electrical activity generated in the subject's muscles is monitored using surface and/or needle recording electrodes. Medical monitoring may take place when a subject is at rest, in motion, or during the performance of a medical procedure. In some cases, medical monitoring involves monitoring the response of the subject to a stimulus. For example, evoked potential (EP) monitoring may be used to detect the electrical response of a subject's brain to audible, visual, or electrical stimuli. Medical monitoring involving stimulus and response detection may be used in combination with EMG and various other medical monitoring methods as well.

Monitoring of the various physiological signals generated by a subject's body is typically performed using dedicated devices and/or systems. For example, EEG monitoring may be performed using a dedicated EEG monitoring system, by attaching electrodes to a subject to detect the electrical potentials of the subject's brain, amplifying and filtering the signals received from the electrodes for the desired frequency range of interest for EEG analysis, and providing the amplified and filtered signals to an EEG analysis system including software for further manipulating the EEG signals for analysis and display on an EEG system monitor. Similarly, EMG monitoring may be performed using a dedicated EMG monitoring system, by placing electrodes on the subject to detect electrical activity generated in the subject's muscles, amplifying and filtering the signals detected by the electrodes for the desired frequency range of interest for EMG signals, and providing the amplified and filtered signals to an EMG analysis system including software for further manipulating the EMG signals for analysis and display on an EMG system monitor. Other signals of interest, e.g., vital signs, may be monitored in a similar manner, with a separate dedicated system provided for each type or modality of monitored signal of interest. Each such dedicated monitoring system may include or be connected to a system for providing stimulus to a subject, and for analyzing the particular detected signal of interest in response to the stimulus provided.

To provide a fall range of diagnostic capability, a doctor's office or operating room, ICU or ER must have available systems for monitoring various physiological signals. Thus, EEG, EMG, vital signs, and other physiological signal monitoring systems preferably must be readily available. Where the capability for monitoring each different type of physiological signal is implemented in a dedicated system, maintaining a full range of diagnostic capability can be a very expensive proposition. Moreover, in many cases it may be desirable to monitor the various physiological signals generated by a subject's body simultaneously. Thus, it may be desired to monitor simultaneously EEG, EMG, vital signs, and other physiological signals generated by a subject. If each type of signal to be monitored requires a dedicated monitoring system, each system having its own set of electrodes, monitoring and display units, etc., all simultaneously connected to a subject, an operating room or other medical facility will be crowded with equipment, which may interfere with the procedures being performed. More significantly, each such system must be operated independently, and may have its own unique user interface. Thus, critical time and effort may be wasted as a physician or other specialist must constantly switch his attention between different medical monitoring systems in order to monitor various physiological signals of interest.

SUMMARY OF THE INVENTION

The present invention provides a medical signal monitoring system and method providing the capability for an operator of the system to display and analyze physiological signals of various types, frequencies, and modalities. The medical monitoring system in accordance with the present invention may be implemented on a conventional computer system having conventional input, output, and disk storage devices. Data input to the medical monitoring system may be provided from various physiological signal acquisition systems, including systems for acquiring electrical physiological signals from electrodes positioned on a subject. Digitized video and audio inputs may also be provided to the medical monitoring system. The medical monitoring system may further be connected to auditory, visual, and/or electrical stimulator systems, for controlling the providing of stimulation to a subject, while analyzing the physiological signals received in response thereto via the acquisition system.

The medical monitoring system in accordance with the present invention employs a data pipeline structure wherein, for example, raw electrical physiological signals from electrodes attached to a subject are both saved and processed. Processing steps which may be performed on the raw electrode signals thus received include defining and generating a signal to be displayed, filtering the signal, defining a trigger signal, averaging the signal, performing spectral analysis and trend calculation of the signal, and displaying the resulting processed signal. Various parameters for each of the processes performed on a signal to be displayed may be established by an operator of the system employing a software user interface implemented in a Windows-type operating system. Since data may be stored as a stream of raw data recorded from an electrode different signals, having different modalities and formats, may be generated and displayed from the stored data, to review the data in a different desired context.

In accordance with the present invention, physiological signals of interest are displayed in panels. The user interface allows different panel types to be selected. The panel type selected determines the basic format of the physiological signal to be displayed. Panel formats preferably are provided for displaying physiological signals as various waveforms and/or as indicators, such as bar indicators.

The signals to be displayed in a panel are defined by selecting, via the user interface, the signals provided by a pair of electrodes, from which a montaged pair signal to be displayed is generated. An operator also employs the user interface to select the modality of the signal to be derived and displayed, e.g., EEG, EMG, or evoked potential (EP). The user interface preferably also provides an operator of the system with the option of displaying signals of interest as triggered, averaged, or trend (compressed) data. Triggering, averaging, and spectral trend data parameters are operator selectable employing the user interface.

Various different panels may be defined by an operator for a particular operator's use, or for a particular patient, or physiological monitoring session. The panels as defined and their associated controls and stimulus parameters may be saved as a template.

During acquisition mode data is received into the data pipeline and displayed in the format defined by the panels. Received physiological signals may also be recorded to disk at this time, and played back at a later time, in the format defined by the panels, to review the data. The source of physiological data provided to the system for display may be a physiological signal acquisition system or a physiological data simulator.

The user interface preferably provides various tools for an operator to use during the display of physiological data in a panel. Such tools may include, for example, the ability to attach comments to displayed signals, the use of cursors and markers to measure the amplitude and latency characteristics of a waveform displayed in a panel, and a look-back tool allowing a portion of a waveform to be frozen for closer examination.

Physiological signals displayed by a medical signal monitoring system in accordance with the present invention may be triggered by stimulus signals provided to a subject via, e.g., electrical, auditory, or visual stimulators. The user interface preferably allows an operator of the system to establish the type of stimulations provided, and the characteristics of such stimulation in a stimulus context. A separate stimulus context may be established for each panel defined by the operator. Stimulus contexts may be different from each other, yet employ the same stimulator rate generators and stimulator systems. Only one stimulus context may be active at a time. A stimulus context is activated by activating a panel. Stimulus context is changed by activating a different panel.

Further objects, features, and advantages of the invention will be apparent in the following detailed description when taken in conjunction with the accompanying drawings.

BRIEF DESCRIPTION OF THE DRAWINGS

FIG. 4 is a screen display showing an exemplary user interface for a medical signal monitoring system in accordance with the present invention.

FIG. 5 is a screen display showing a pull-down menu of the user interface of FIG. 4, showing different panel types available for displaying signals in different formats in a medical signal monitoring system.

FIG. 6 is a screen display showing a user interface for defining the signals associated to an amplifier device to be displayed in a panel.

FIG. 7 is a screen display showing a user interface for defining digital filtering to be applied to a signal to be displayed.

FIG. 8 is a screen display showing a user interface for defining triggering and averaging parameters for a signal to be displayed.

FIG. 9 is a screen display showing a user interface for defining a trend signal to be displayed.

FIG. 10 is a screen display showing a user interface for defining the general characteristics of a signal to be displayed in a panel.

FIG. 11 is a screen display showing a user interface for selecting a data source to be used during an acquisition mode.

FIG. 12 is a screen display showing examples of panels displaying physiological signal data in different forms.

FIG. 13 is a screen display showing a user interface for finding a comment that was associated with or connected to signals being displayed.

FIG. 14 is a screen display showing the use of cursors for measuring a wave form being displayed.

FIG. 15 is a screen display showing use of markers for measuring a wave form being displayed.

FIG. 16 is a screen display showing use of a look-back function for viewing a portion of a wave form being displayed.

FIG. 19 is a screen display showing an exemplary user interface for establishing a stimulator context for a medical monitoring system in accordance with the present invention.

FIG. 20 is an exemplary screen display showing the display of various stimulation triggered physiological signals.

DETAILED DESCRIPTION OF THE INVENTION

Figure 1:
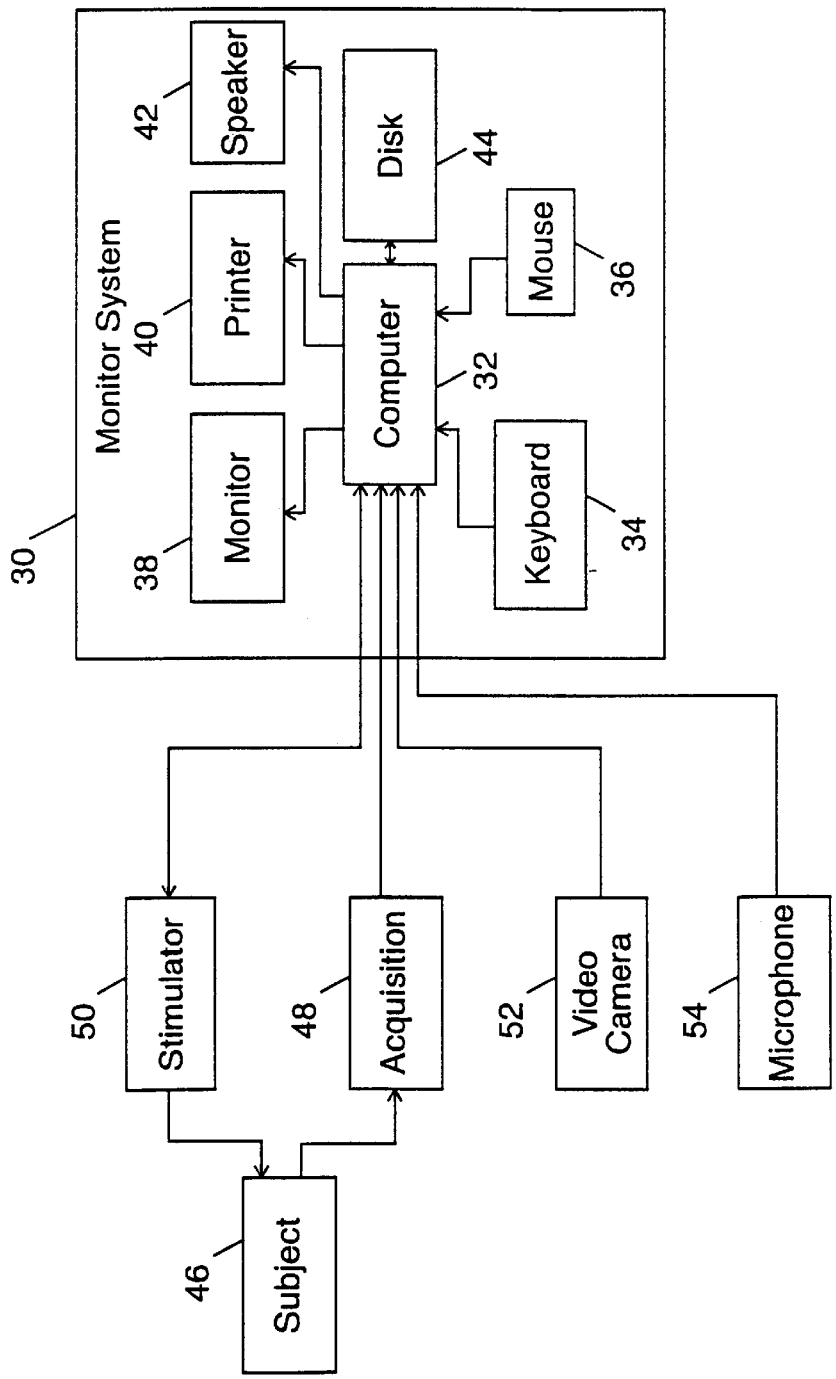
FIG. 1 is a schematic block diagram of an exemplary medical signal monitoring system in accordance with the present invention.

The present invention provides an integrated medical signal monitoring system, allowing a physician or other operator to display and monitor simultaneously various different types of physiological signals recorded from a subject. The present invention provides an integrated flexible user interface, which allows an operator of the system to define the manner of interaction and to control the information which will be displayed and analyzed, as well as to control the providing of stimulation to a subject when the determination of the physiological response of a subject to stimulus signals is desired.

A basic hardware configuration for a medical signal monitoring system 30 in accordance with the present invention is illustrated in, and will be described with reference to, FIG. 1. A medical signal monitoring system 30 in accordance with the present invention may be implemented using a conventional computer system having conventional computer peripheral devices. For example, monitoring system 30 may be implemented on a conventional personal computer 32. Due to the large number of computations performed by the computer 32, a computer employing a very fast processor, such as a Pentium 200 MHz processor, or faster, is preferred. It should be understood that the present invention may be implemented using other types of general purpose programmable computers 32.

The computer 32 is preferably provided with conventional computer peripherals. For example, the computer 32 preferably includes conventional input devices such as, for example, a keyboard 34 and a mouse 36. Other types of input devices, such as a microphone for voice recognition control of the system, may be employed. Conventional output devices which may be employed with the computer 32 include a computer monitor 38, printer 40, and speaker 42 for providing audio output from the computer 32. The computer 32 is preferably also provided with a large disk storage capability 44.

The monitoring system 30 receives physiological signals from a subject 46 via one or more signal acquisition systems 48. The signal acquisition systems 48 may be connected to the subject by, for example, electrodes placed on the subject 46. The electrodes provide electrical physiological signals to the acquisition systems 48. The acquisition systems 48 amplify the signals received from the electrodes 46, provide some preliminary filtering of the signals, and then provide the amplified and preliminarily filtered signals to the monitoring system 30 for analysis and display. In a dedicated EEG or EMG system, the acquisition systems 48 may filter the electrode signals to a relatively narrow band of interest. However, the present invention provides a system for the display of signals across a broad frequency range. Thus, a broad band of frequencies should be passed by the acquisition systems 48 (e.g., at least broad enough to include the EEG and EMG bands). The signals provided to the monitoring system 30 are, therefore, essentially raw signals.

The monitoring system 30 preferably also controls the providing of stimulation signals to the subject 46 via one or more stimulator systems 50. Various different types of stimulator systems 50 may be employed, including stimulator systems 50 for providing electrical, auditory, or visual stimulation. The stimulator systems 50 may be connected to the subject 46 via, for example, electrodes, for providing electrical stimulation to the subject, headphones, for providing auditory stimulation to the subject 46, or goggles including LEDs mounted thereon, for providing visual stimulation to the subject 46. The stimulator systems 50 preferably provide a signal back to the monitoring system 30 indicating the time at which a stimulation signal is provided to the subject. This signal allows the monitoring system 30 to synchronize the stimulation signals provided to the subject 46 with response signals received from the acquisition systems 48 for proper analysis and display of the relationship between the stimulus and response signals.

Other signals, such as video signals from a video camera 52, and sound signals from a microphone 54, may also be provided to the monitoring system 30. Conventional methods for digitizing the video and audio signals provided by the video camera 52 and microphone 54 for use by the monitoring system 30 may be provided.

It should be understood that each of the hardware components illustrated in FIG. 1 may be implemented in a conventional manner, using conventional commercially available hardware devices. Also, the various hardware systems illustrated in FIG. 1 may be connected together in a conventional manner, using conventional cabling, connectors, etc. Alternatively, the various hardware systems illustrated in FIG. 1 may be connected together via a network bus topology, such as, for example, an IEEE 1394 high-speed serial bus topology. In the later case, the stimulus signals provided by the stimulator devices 50 and the response signals detected by the acquisition systems 48 may be time frame synchronized in the manner described in a co-pending U.S. patent application Ser. No. 09/320,613 entitled TIME FRAME SYNCHRONIZATION OF MEDICAL MONITORING SIGNALS.

Figure 2:
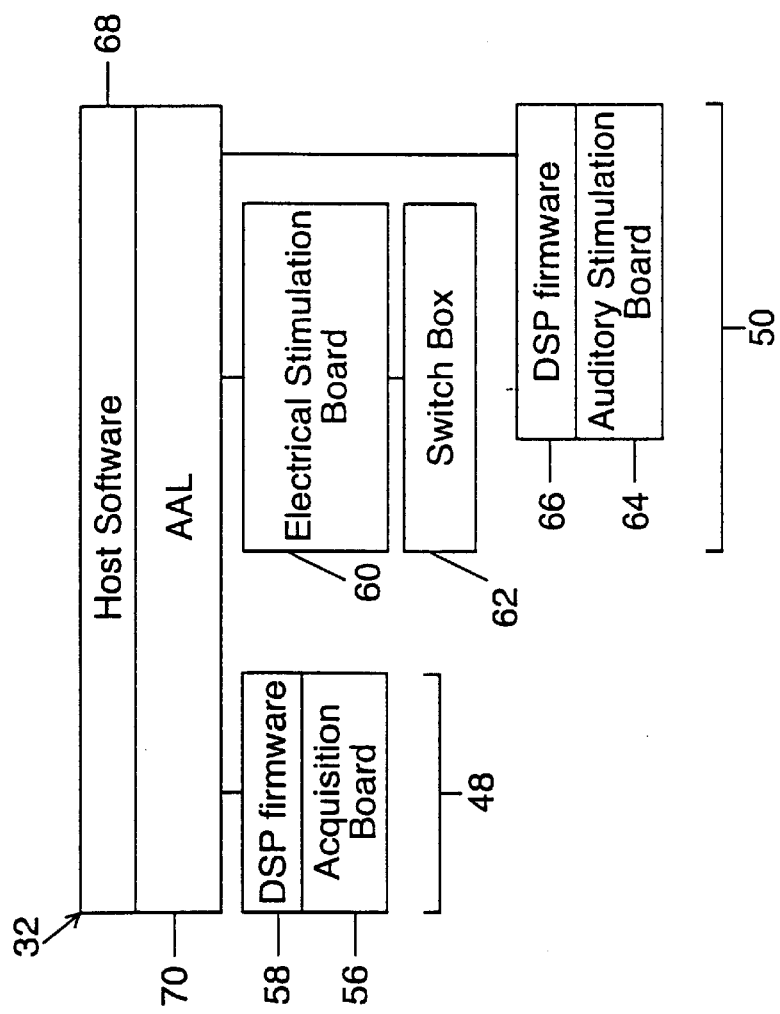
FIG. 2 is a schematic block diagram illustrating an exemplary interface between signal acquisition and stimulation systems and a medical signal monitoring system in accordance with the present invention.

The interface of signal acquisition systems 48 and stimulator systems 50 with a monitoring system 30 in accordance with the present invention is described in more detail with reference to the schematic block diagram of FIG. 2. The acquisition system 48 may include, for example, an acquisition board 56 into which the various signals from electrodes attached to the subject 46 are provided. The acquisition board 56 includes digital signal processor (DSP) firmware for converting the electrode signals into a format for transmission to the monitoring system computer 32 for analysis and display. The stimulator system 50 may include, for example, an electrical stimulation board 60, which receives signals from the monitoring system computer 32 controlling, for example, the magnitude, duration, and location of electrical simulation signals to be provided to the subject 46. The electrical stimulation board 60 is connected to the electrodes attached to the subject 46 via a switchbox 62, whereby the electrodes to which electrical stimulation signals are to be provided are selected. Auditory stimulation may be provided to the subject 46 via an auditory stimulation board 64. The auditory stimulation board 64 is connected to the monitoring system computer 32 via DSP firmware 66 which converts control signals from the computer 32 defining the auditory stimulation to be provided to the subject 46 into the desired analog signals. (Similarly, a visual stimulation board, including DSP firmware, may be provided for visual stimulation.)

Low level host software 68 (kernel driver or library) running in the monitoring system computer 32 provides the interface to the acquisition 48 and stimulation 50 systems. The host software 68 provides the basic I/O interface between the DSP firmware 58 in the acquisition board 56, the electrical stimulation board 60, and the DSP firmware 66 in the auditory stimulation board 64 (and/or a visual stimulation board). The details of the host software 68 to be employed will depend upon the nature of the signals to be received from and provided to the acquisition 48 and stimulation 50 systems. The host software 68 provides the initial software interface between the acquisition 48 and stimulation 50 systems and the higher level software running in the monitoring system 30 for the analysis and display of the physiological signals received from the acquisition system 48, and control provided to the stimulation system 50. Although the host software 68 may require modification for different acquisition 48 and stimulation 50 systems which may be employed with the monitoring system 30 of the present invention, it is preferred that the higher level software running in the monitoring system 30 not need to be modified for use with different acquisition 48 and stimulation 50 systems. Thus, an acquisition abstraction layer (AAL) 70 is preferably implemented in the system computer 32 to provide an interface between the host software 68 and the higher level analysis, display, and control software running in the monitoring system computer 32. The AAL may be implemented in software in a conventional manner to allow for easy substitution of acquisition 48 and stimulation 50 systems, and corresponding low-level host software 68, without requiring modification of the higher level software running in the computer system 32. Details of implementing the AAL depend on the implementation of the host software 68 and the higher level display, analysis, and control software running in the monitoring system computer 32.

A medical signal monitoring system 30 in accordance with the present invention employs a simplified data pipeline concept which facilitates flexible data storage, replay, analysis, display, and synchronization. An exemplary data pipeline 72 in accordance with the present invention will be described with reference to the schematic flow chart diagram of FIG. 3. Physiological signals from a subject are provided to the data pipeline 72 in essentially raw form. Thus, the data entering the data pipeline 72 may be, for example, the raw electrical signals detected by electrodes 74 attached to the subject 46. (It should be understood that basic processing such as signal amplification and some initial filtering may be provided by the acquisition system 48, as described previously, before the "raw" data signals are provided to the data pipeline 72.) The "raw" data entering the data pipeline 72 includes both physiological signals acquired by the acquisition system 48 as well as the timing signals provided by the stimulator system 50 indicating the providing of a stimulation signal to the subject 46.

The raw data entering the data pipeline 72 is provided initially along two paths, one for storage of the data, the other for display and analysis of the data. The raw data entering the data pipeline may be stored to disk 76. Simultaneously, the raw data entering the data pipeline is provided along the display and analysis path, where various processes are applied to the raw data signals. Such processes include, for example, montaging 78, wherein, for example, the signals provided from two electrodes 74 are combined in a desired manner to form a montaged pair 80. The montaged pair signal 80 may then be filtered with, e.g., a band pass filter for a desired frequency range of interest. In addition, variable band reject filtering may be applied to attenuate undesirable signals within a certain frequency range. The filtered signal 82 may be triggered 84 to be displayed in response to the appearance of a desired trigger condition. The signal may be averaged 86 before it is displayed. Spectral analysis of the signal may be performed, for example, by performing a Fast Fourier Transform (FFT) calculation 88 on the signal. Further calculations may be performed to determine and display the trend of the signal data 90. As will be described in more detail below, each of these processes applied to the signals to be displayed are operator selectable, and employ parameters which are user selectable by an operator employing a user interface.

At any point along the data processing pipeline 72, the processed signal may be displayed 92 on the system monitor 38. This will be described in more detail below. Also, at any point along the data pipeline 72, the processed signal may be saved to disk 44. For example, the averaged 94 and/or trend 96 signal may be saved to disk.

Figure 3:
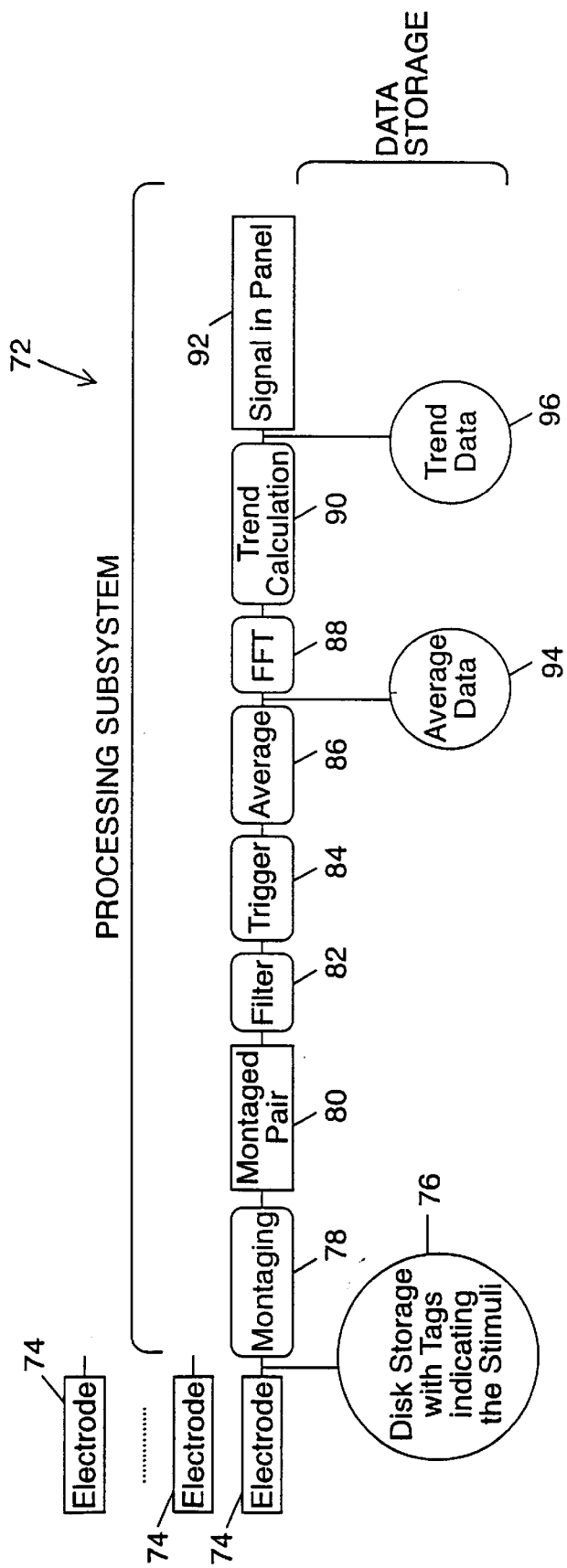
FIG. 3 is a schematic diagram illustrating a data pipeline employed in a medical signal monitoring system in accordance with the present invention.

The data pipeline concept 72 illustrated in FIG. 3 is particularly useful in a medical signal monitoring system in accordance with the present invention. Raw data from the acquisition 48 and stimulator 50 systems may be either stored to disk 76 or passed along the data pipeline 72 for processing for analysis and display, or both simultaneously. The processing steps performed on the signal as it passes along the data pipeline 72 may be performed in any order, although montaging of data 78 to generate a montaged pair 80 is preferably the initial data processing step performed. Also, as discussed previously, a processed signal may be displayed and/or saved at any point along the data pipeline 72. The parameters employed for montaging, filtering, triggering, averaging, frequency analysis, and trend calculations are all preferably operator selectable. Also, the format in which the processed signal is displayed is preferably operator selectable. As will be described in more detail below, the present invention provides a user interface which facilitates the selection of each of these parameters and display formats.

The saving of raw signal data 76 to disk 44 is significant. This allows reanalysis and display of the data at any time using entirely different processing parameters. For example, upon initial processing, the signals provided by two electrodes may be montaged and processed to provide an EEG signal for analysis and display. At a later time, it may be desired to analyze an EMG signal between the first electrode and a third electrode located on the subject 46. Since the raw signal data from all of the electrodes is available on disk 44, the signals from the first and third electrodes may be montaged and processed to provide the desired EMG signal for analysis and display. Since incoming signal data is stored and/or processed as it is received, synchronization between the different signals generated for analysis and display therefrom is automatic.

Figure 4:
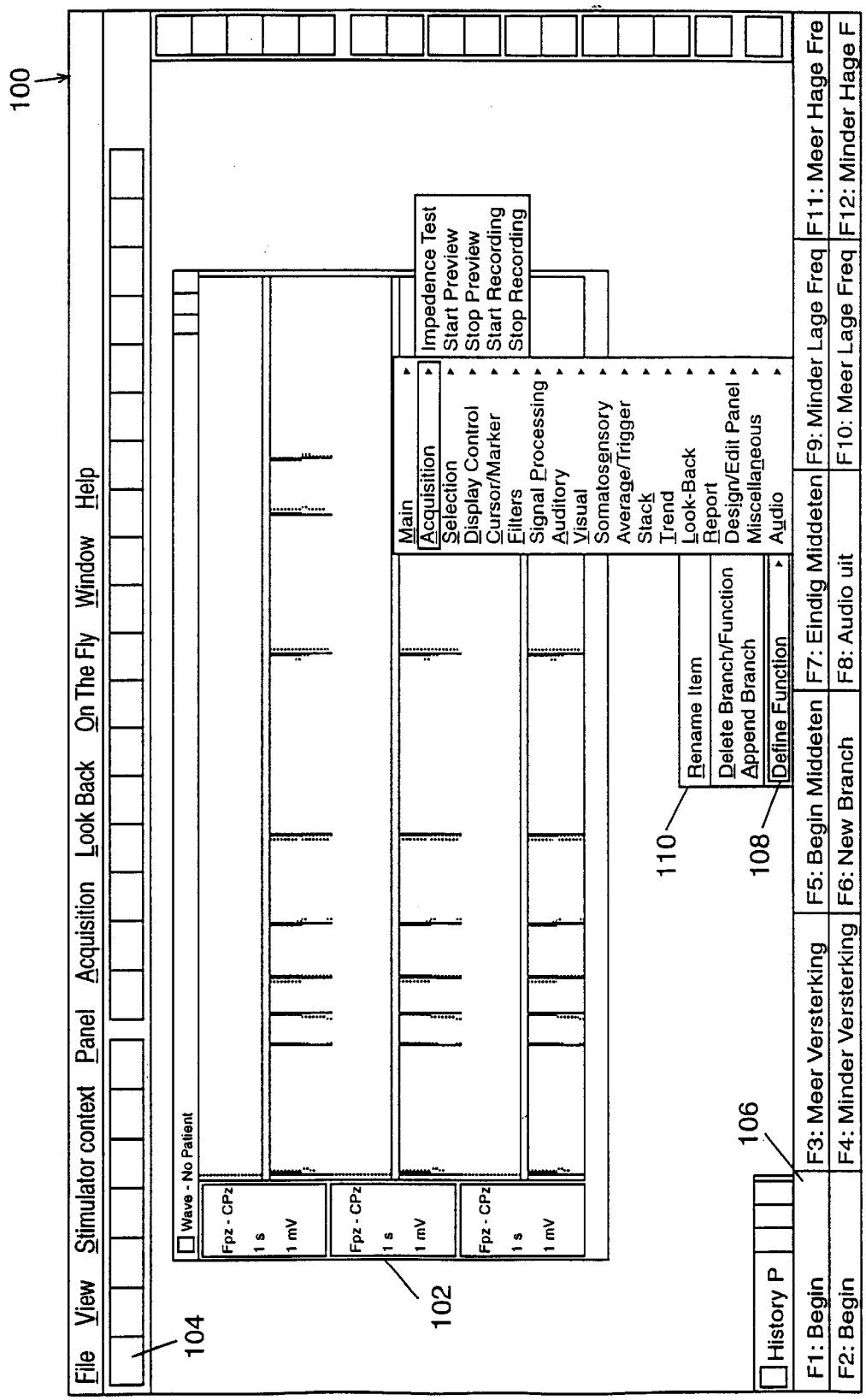
FIGS. 4–16, 19, and 20 are exemplary screen displays generated by a medical signal monitoring system in accordance with the present invention.

A user interface for controlling the signal analysis and display features of a medical signal monitoring system 30 in accordance with the present invention preferably is implemented in software in the system computer 32 using a Windows-type operating system. A basic exemplary user interface and display screen 100, which may be displayed on the computer monitor 38 of a medical signal monitoring system 30 in accordance with the present invention, is illustrated in FIG. 4. The basic user interface and display screen 100 includes two basic components. Physiological signals to be displayed to an operator of the system 30 are presented in one or more windows 102 in the center part of the screen 100. As will be described in more detail below, each such window 102 in which physiologic signal data is displayed will be referred to as a panel. Different panels may be used to show different signals and/or different forms of signals. The signal display panel 102 includes the signal being displayed as well as appropriate labels for the signal.

In the margins of the screen 100 various buttons, pull-down menus, etc., are provided which form the user interface 104. The user interface 104 is implemented as a basic mouse/keyboard controlled Windows-like user interface. The various functions of the user interface 104 may be accessed, for example, by selecting features using the mouse 36. Additionally, keyboard shortcuts for certain functions are preferably operator definable. For example, each function key on the keyboard 34 may be assigned a user interface function. The functions assigned by the operator to each function key on the keyboard 34 are preferably displayed 106 on the user interface screen 100. A mouse-controlled menu 108 is preferably accessible by an operator to assign functions to each function key 106. A default name of the function may be assigned to the function key and displayed on the screen 106. Alternatively, the operator is preferably given the option of renaming 110 the function displayed in association with each key at 106. Thus, a function may be named with a label recognizable by a particular user. For example, a function assigned to a function key may be named in the native language of a user of the system. This allows common functions to be easily accessible by operators in various different languages, without requiring a complete reworking of the user interface into a different language. Note that the function keys on the keyboard 34 may be color-coded, with the corresponding display 106 of the functions assigned to each function key displayed on the screen 100 in the corresponding color.

Use of a medical signal monitoring system 30 in accordance with the present invention begins with a set-up procedure or mode wherein the operator of the system 30 defines the data of interest to be displayed on the system 30 and a format in which the information is to be displayed. In accordance with the present invention, physiological signals are displayed in windows called panels on the operator display 100. Preferably various different types of panels are available to an operator of the system 30, and multiple panels may be defined for a particular operator, patient, or monitoring session. A set of panels with associated user interface and stimulation parameters defined by an operator during the set-up phase or mode may be saved as a template.

Figure 5:
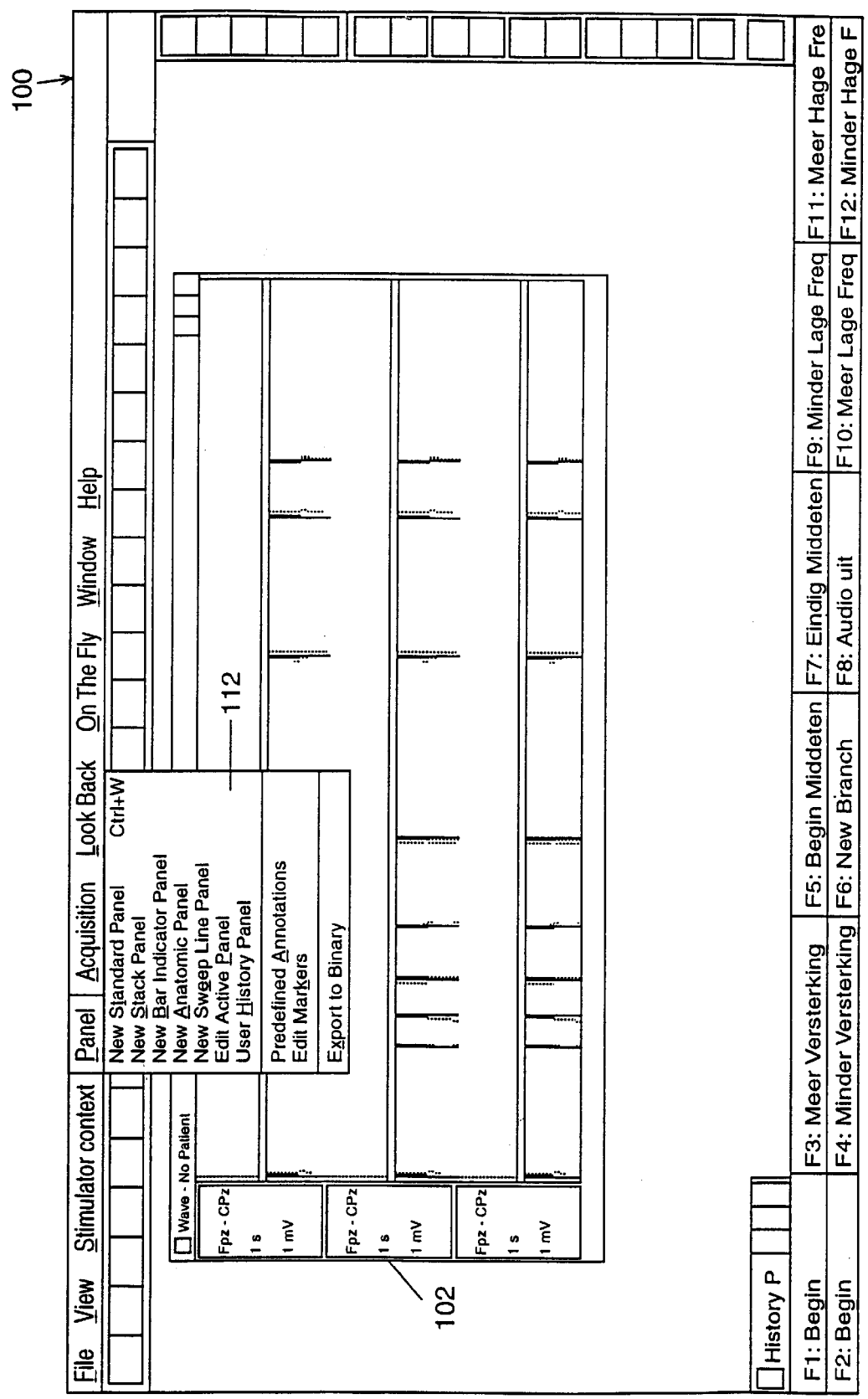

After defining stimulus contexts, if any, as described in detail below, an operator of the system 30 continues the set-up process by selecting a panel type. The panel type defines the basic format in which the physiological signal data will be displayed. As illustrated in FIG. 5, a variety of different panel types which may be available to an operator of the system 30 include standard panels, stack panels, bar indicator panels, anatomic panels, and sweep line panels. Standard panels, sweep line panels, and stack panels are defined as wave panels, in which signal waveforms are displayed. In a standard panel waveform data scrolls from right to left, in a sweep line panel waveform data goes from left to right in an oscilloscope type fashion in a stack panel waveforms are displayed in columns preferably scrolling from bottom to top. Each of these wave panel types will be described in more detail and illustrated as this detailed description proceeds.

In addition to wave panels, other panel types allowing the display of data in other formats may be provided. For example, an operator of the system 30 is preferably given the option of defining a bar indicator panel to display, for example, the instantaneous amplitude or area under a curve of a selected signal. An exemplary bar indicator panel display will be described and illustrated in more detail below. Another type of panel which is preferably made available to an operator of the system 30 is an anatomic or map panel. In an anatomic panel, for example, the same parameters that can be displayed in the bar indicator panel can be displayed, for example, as a bar or circle, superimposed on a diagram of a human body in a color-coded fashion. A color scale, as is used in the bar indicator panel, may be employed. The diagram of a human body may be a bit map provided with the system 30 or by the operator. Using a pointing device, such as the mouse 36, an operator of the system 30 is preferably able to reposition the indicators on the bit map during run-time, and save the new layout during the set-up procedure.

Figure 6:
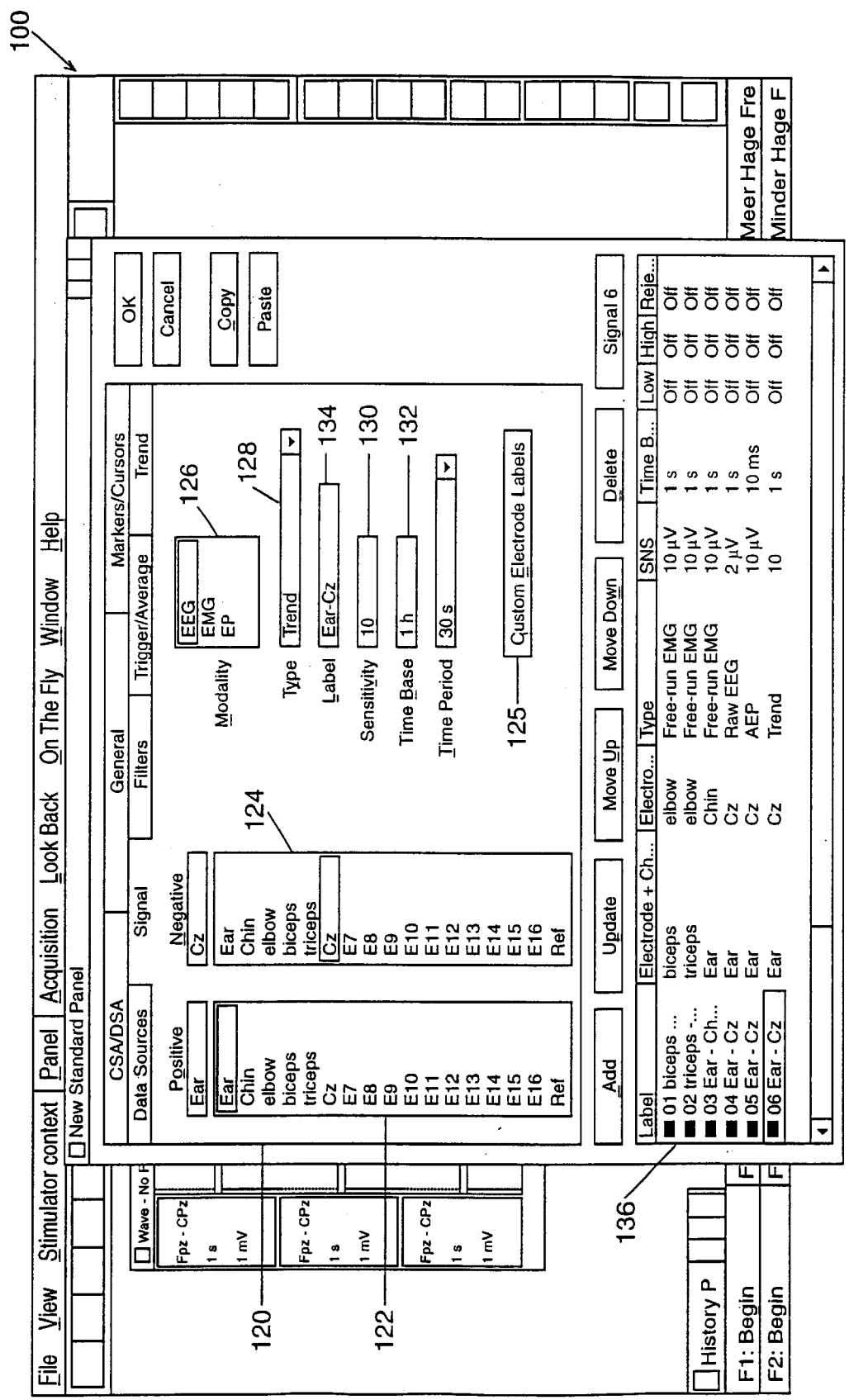

Having selected a panel format in which physiological signal data is to be displayed, the system user interface allows an operator of the system 30 to define the signals which will be displayed in the panel. An exemplary user interface 120 for allowing an operator of the system 30 to define the signals to be displayed in a panel is illustrated in FIG. 6. For electrical physiological signals, for example, the signals to be displayed are defined in terms of electrodes positioned on the body of a subject 46. A set of electrodes are positioned on a subject's body, at various locations, to detect the electrical signals generated thereby. The electrodes may be labeled E1, E2, E3, etc. A user of the system 30 may re-label the electrodes 125, perhaps based on the position of the electrode on a subject's body. For example, ear, chin, elbow, biceps, triceps, and Cz, electrodes are labeled as such in the exemplary user interface 120. A signal to be displayed in a panel is defined by selecting a positive 122 and a negative 124 electrode signal from those available. For example, FIG. 6 shows the selection of a signal to be displayed which is defined by the ear electrode as the positive electrode signal source and the Cz electrode as the negative electrode signal source. The signal may be displayed as a montaged pair signal derived from the raw electrical signal provided to the data pipeline via the acquisition system 48 from the ear electrode and the raw electrode signal provided to the data pipeline via the acquisition system 48 from the Cz electrode.

Having identified the electrodes from which the signal to be displayed will be derived, an operator may then select the modality 126 of the signal to be displayed. In the exemplary embodiment shown in FIG. 6, an operator of the system is able to select between EEG, EMG, and EP modalities. Other or different modalities may also be provided. The modality selected defines the filtering and other processing which will be applied to the electrode signals defined by the user before the signal is displayed.

Having selected the modality of the signal to be displayed, the operator of the system 30 may further define the type of wave form 128 to be displayed. The available types of wave forms may depend on the modality selected. Exemplary types of waveform signals to be displayed may include, for example, raw EEG, CSA, DSA, EEG-trend, free run EMG, triggered EMG, averaged triggered EMG, stimulated EMG, averaged stimulated EMG, and auditory, visual, and motor evoked potential EP), etc.

The operator of the system 30 may preferably also set the display sensitivity value 130 for the signal to be displayed, and the time base (amount of seconds or milliseconds per panel) of the displayed signal 132.

A signal to be displayed, as just defined by the operator of the system 30, may be assigned a default label by the system. For example, the default label may be the pair of electrodes defining the signal. However, the user is preferably able to override the assigned label in order to assign custom labels 134.

Multiple signals to be displayed in a panel may be defined in the manner described. The signals to be displayed in a panel thus defined are listed in a portion 136 of the user interface window 120 wherein the signals to be displayed in the panel are defined. As illustrated by the example in FIG. 6, six signals to be displayed have been defined for a standard wave panel. The sixth signal thus defined is defined by a montaged pair to be derived from electrodes placed at the ear and Cz of a patient. The selected modality for the signal is EEG, and the type of signal to be displayed is a trend wave form. The display sensitivity has been set at a value of ten, with a time base for the display of one hour. FIG. 6 also illustrates, by example, five other signals which have been defined for display in this standard wave panel.

Figure 7:
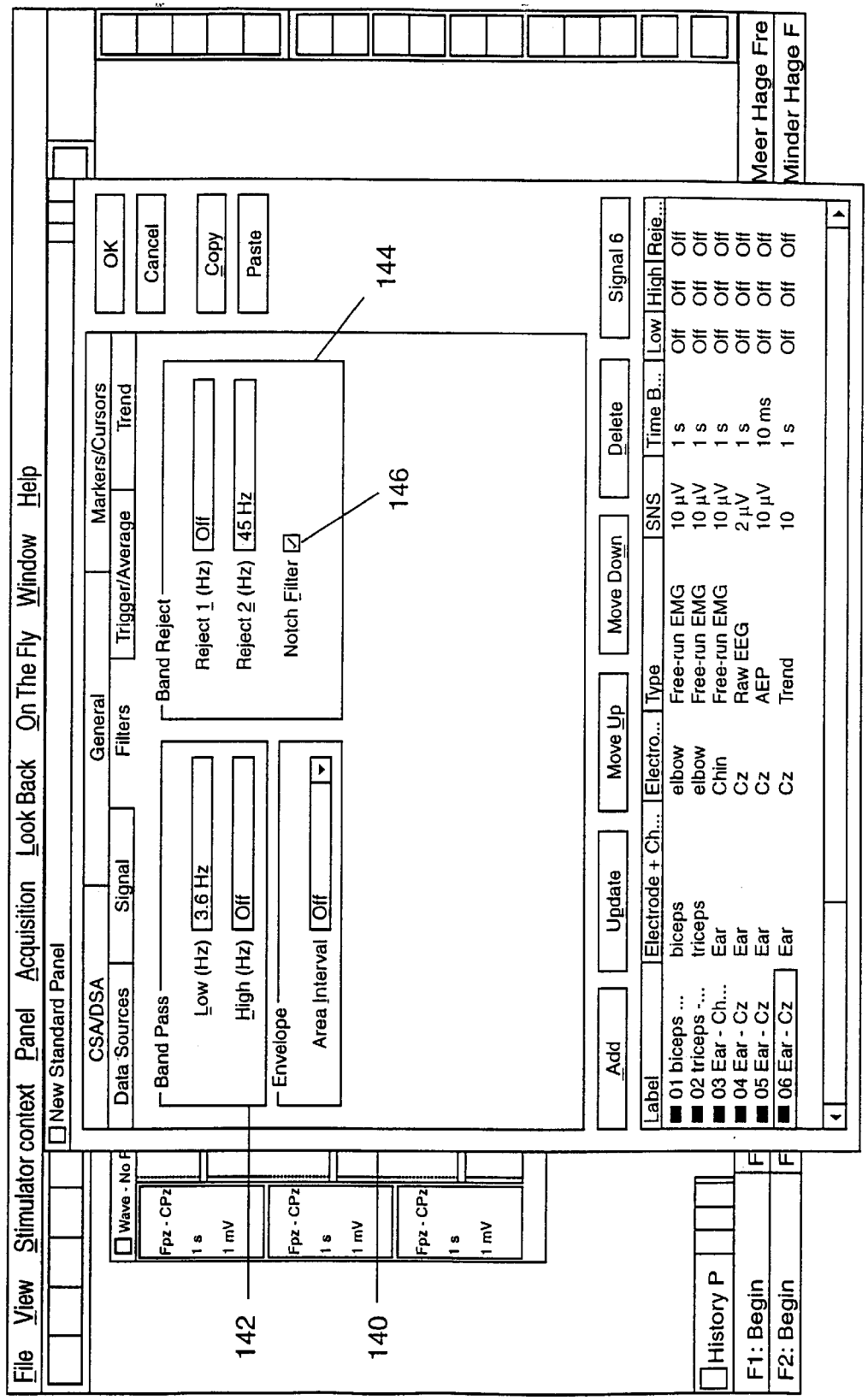

In accordance with the present invention, an operator of the medical signal monitoring system 30 is preferably able to control the filtering to be applied to the signals displayed in a panel (i.e., the montaged pair signal). An exemplary user interface for providing such filter selection is illustrated at 140 in FIG. 7. Band pass filtering of the signal to be displayed may be defined by selecting desired low and high cutoff frequencies 142. Band pass filtering of the signal to be displayed may be implemented in software. An operator of the system 30 is preferably also able to select band-reject frequencies for the signal to be displayed. For example, a portion 144 of the user interface preferably allows an operator of the system to select one or more band-reject frequencies. Band-reject filtering of the signal to be displayed may be implemented in software, for example, as Butterworth band stop filters. Notch filtering of power line noise (e.g., at 50 or 60 Hertz) is preferably provided by the system 30. An operator of the system 30 is preferably given the option of turning on or off the notch filter by selecting a box 146 provided in the user interface 140.

Figure 8:
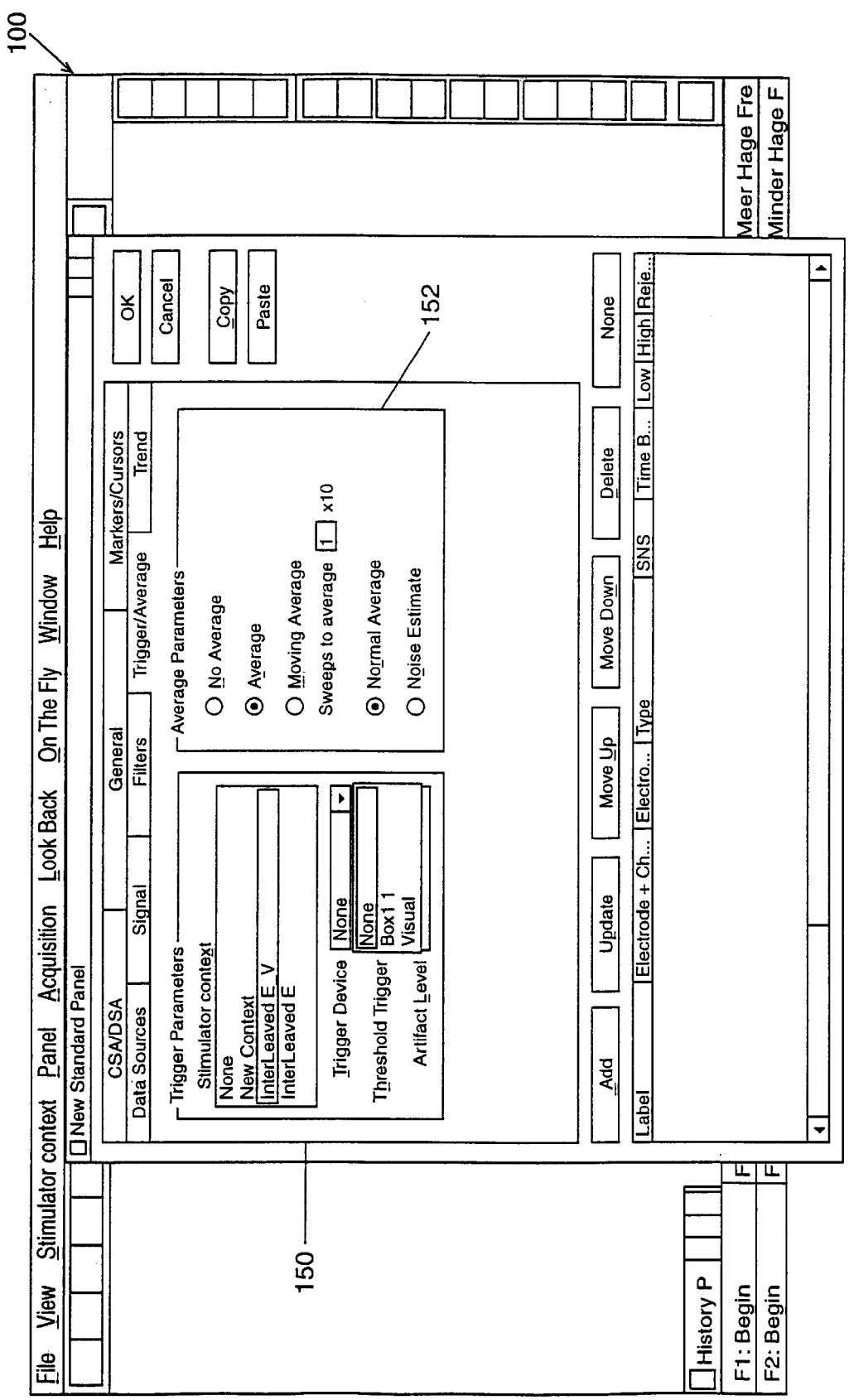

As discussed above, a signal to be displayed by a medical signal monitoring system 30 in accordance with the present invention may be a triggered signal. As illustrated, for example, in FIG. 8, a portion of the user interface 150 preferably allows an operator of the system 30 to define the trigger for the triggered signal to be displayed. A triggered signal to be displayed may be triggered off of a stimulator signal, a trigger device, or a threshold level of the signal. (Further details on establishing a stimulator context for the signals displayed in a panel will be discussed below.) Thus, triggered signals to be displayed may be synchronized with a stimulator or with a level of the wave form (an operator definable level of triggering).

The user interface of a medical signal monitoring system 30 in accordance with the present invention preferably also provides a user interface 152 for defining an averaged signal to be displayed. An averaged signal is a special case of a triggered signal. In an averaged signal, the signal data is averaged over a period of time and the resulting averaged wave is displayed. As illustrated in FIG. 3, averaged data may be saved separately. The averaged data may be stored into a buffer. Two types of buffers may be provided, the sum of odd and even (normal average) and the difference of odd and even (noise estimate).

Data may be averaged starting at a trigger point, or, where the signal is triggered from a stimulus signal, with a pre-stimulus period. The maximum duration of the pre-stimulus period may be set equal to the duration of the post-stimulus period. Two types of averaging may be provided. In the first type of averaging, each new averaging period starts from scratch. Once an averaging period is completed, the results stay on the operator display screen until the operator restarts the averaging. A separate average pause/resume function may be provided to temporarily stop an averaging function. The second type of averaging is a moving average. A moving average is used to update data in a fast way. For example, the number of repetitions may be divided into a number of sub-averages (e.g., 10). Every completion of a new sub-average is added to the total after the first is subtracted. The total wave form is then displayed to an operator of the system 30. Averaging of a signal can be used in combination with electrical, visual, or auditory stimulation.

Artifact detection is provided to reject or accept sweeps contributing to the end result averaged signal to be displayed. An artifact state is defined if the signal exceeds a set sensitivity. Artifact detection is tied to individual input channels. If an artifact is detected in a channel, the trace is not added to the average or sub-average. The artifact part of a wave form may also be shown differently as a dotted line. When an averaged wave is displayed, the number of required periods, number of rejected periods, and type of average (normal or noise estimate) is preferably displayed along with the averaged wave form. Preferable a new average is scheduled every X minutes, where the value of X is under operator control.

Figure 9:
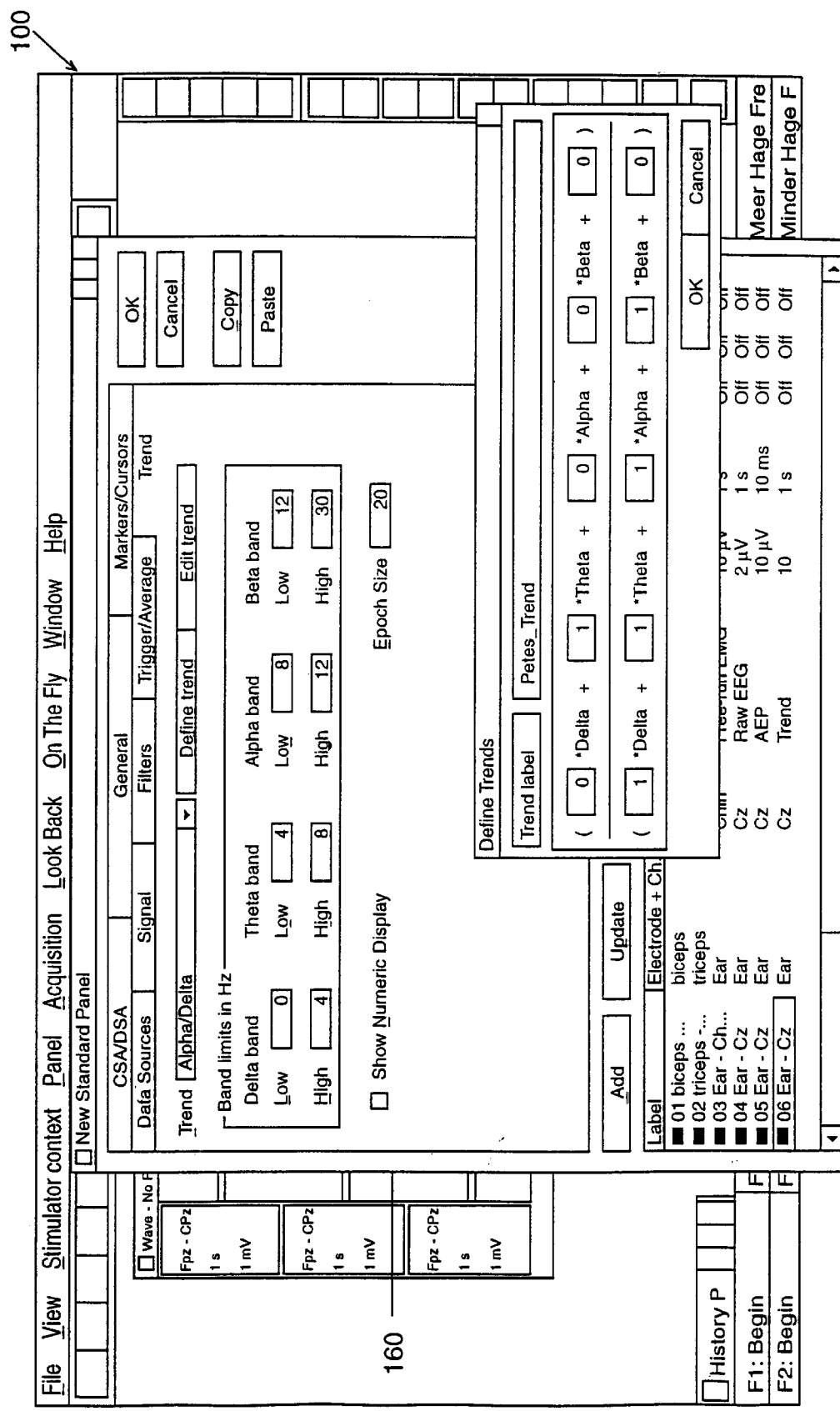

As mentioned previously, a signal to be displayed in a wave panel may be displayed as a trend wave form. Preferably any type of monitored medical signal may be displayed as a trend, e.g., EEG, EP, or vital sign signals. For example, EEG trends may be based on the spectral parameters of a signal. Spectral bands are preferably operator definable and composed into any type of index. Preferably a portion 160 of the user interface, as illustrated, by example, in FIG. 9, allows operator selection of the spectral bands. For example, the user interface 160 may allow construction of coefficients in the form of: $(a1b1+a2b2+a3b3+a4b4+a5)/(c1b1+c2b2+c3b3+c4b4+c5)$ where the bands b1 to b4 may be designated as Delta, Theta, Alpha and Beta. The coefficients $a_i$ and $c_i$ are also preferably operator definable. For evoked potential (EP) measured values, the trend plots can be for x-axis/y-axis displayed in various scales, such as linear/linear, linear/log, or linear/dB. For the dB scale, the plotted value y is calculated using: $y=C \log(\text{value}/\text{reference value})$ with C=constant. The reference value is preferably also operator definable.

Figure 10:
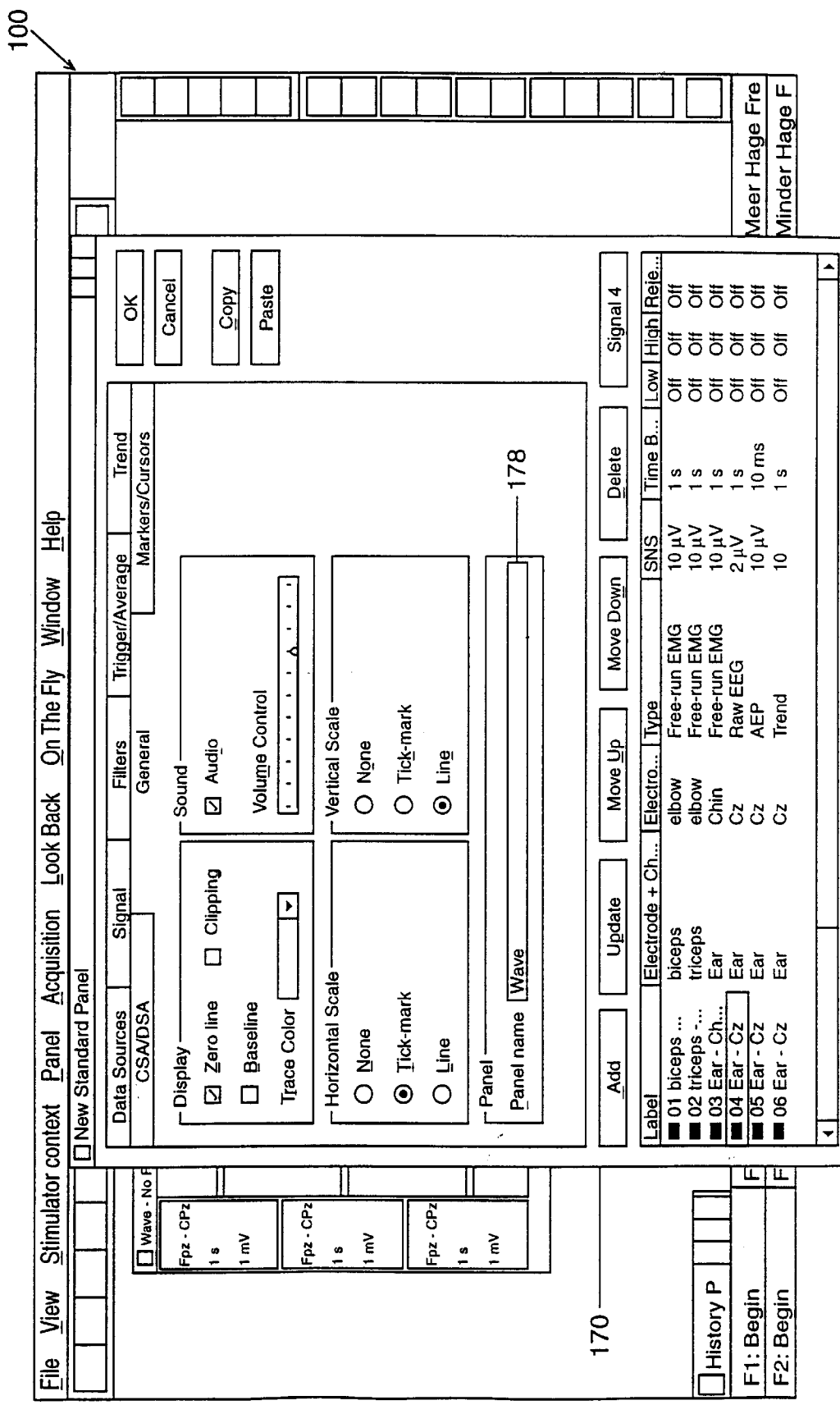

A portion 170 of the user interface, as illustrated, by example, in FIG. 10, preferably allows an operator of the system 30 to define other general characteristics of the signals to be displayed in a panel. Such user selectable features may include: whether or not a zero line is to be displayed in association with each trace, whether or not a wave to be displayed in a panel has a full panel or only part of the panel (total panel height/number of traces) allotted for the wave (clipping), whether or not a selected baseline is to be shown in the background of a wave form, the color of the waveform trace to be displayed, whether or not a sound representation of the signal is to be provided on the system speaker 42, and if so, what percentage of the displayed signal is included in the sound, and whether or not horizontal and vertical scales are to be provided, and if so, how they are to be indicated, e.g., as tick-marks or lines. An operator of the system 30 is preferably also able to define 178 the name of the panel in which signals are to be displayed. Other or different general features of this type may also be provided for formatting a signal to be displayed in a panel.

One or more panels may be defined in the manner described, and saved as a template. Different templates may be created for different operators, patients, monitoring sessions, etc. When data acquisition begins, one of the created templates is selected for displaying the data. Thus, once the set-up procedure has been performed, it need not be repeated unless another template is to be created or an existing template edited.

Figure 11:
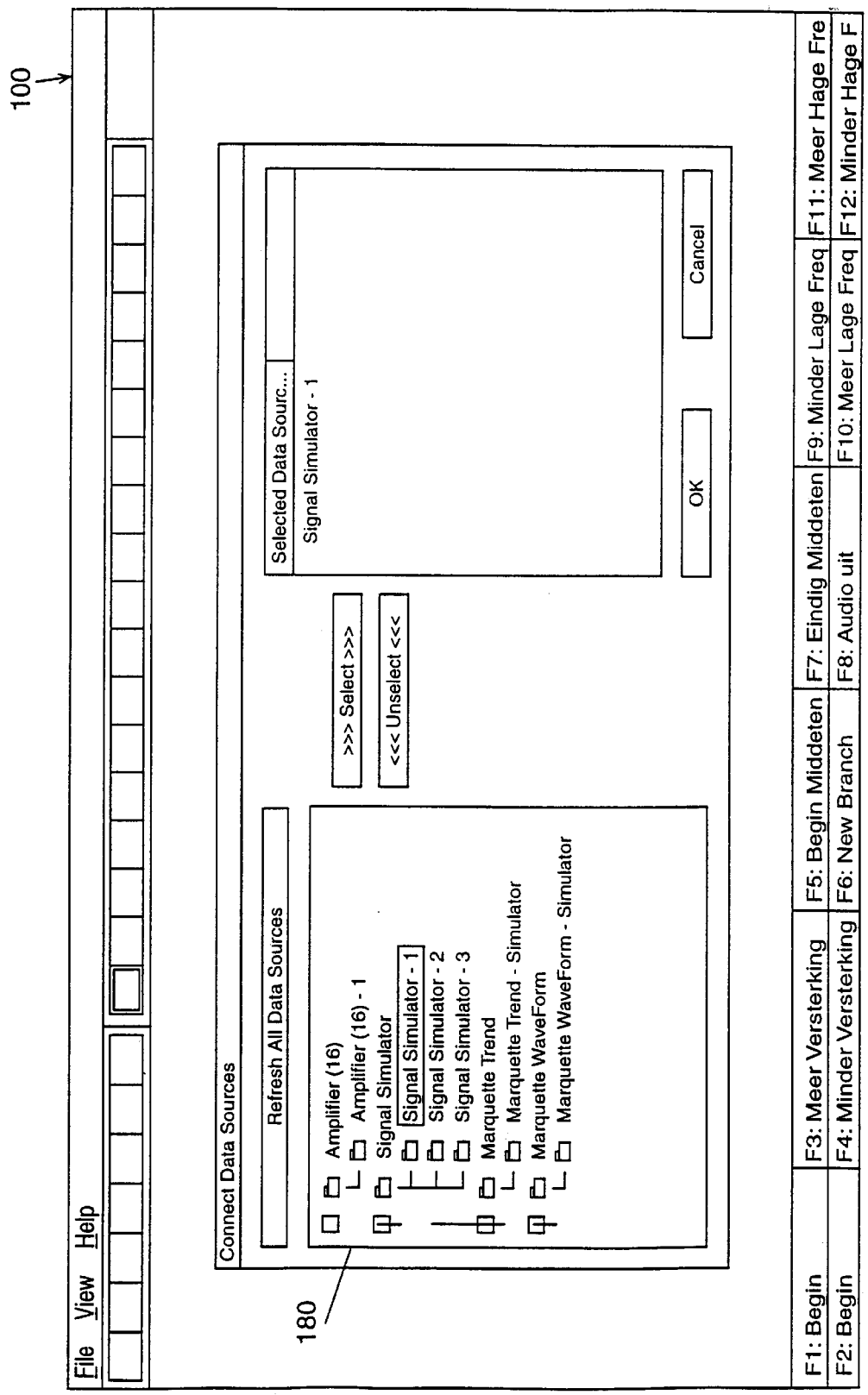

Having defined the physiological signals to be displayed, by defining one or more panels and the signals to be displayed therein, raw physiological signals, e.g., signals from electrodes attached to a subject 46 and provided to the monitoring system 30 via acquisition hardware 48 may be provided to the monitoring system for display and analysis. As illustrated in FIG. 11, the user interface preferably provides an interface 180 to the operator of the system 30, allowing the operator of the system 30 to select the source of data which will be provided to the system 30. For monitoring the physiological signals provided by a subject 46, the acquisition system 48 (i.e., amplifiers) attached to the monitoring system 30 may be selected. Alternatively, simulated physiological signals, e.g., from one or more signal stimulators, may be selected as the data source. Simulated physiological signals may be employed, for example, to refine the display set-up of the wave forms to be displayed by an operator, or to test or calibrate the system 30. Beside "live" data, from either an acquisition system 48 or a simulator, an operator of the system may also review raw physiological signal data which has been stored on a disk 44.

As discussed previously, during the set-up mode an operator of a medical signal monitoring system 30 in accordance with the present invention defines the signals which are to be displayed and analyzed by the system 30. During an acquisition mode, physiological data of different modalities is displayed and/or recorded by the system. Preferably at least two acquisition modes are available to a user of the system. During a preview mode, raw physiological data is fed to the system (through the data pipeline 72) for analysis and display, but is not saved to disk. During record mode, raw physiological data is provided through the data pipeline 72 for analysis and display, and is simultaneously saved to disk 44 for later review.

Figure 12:
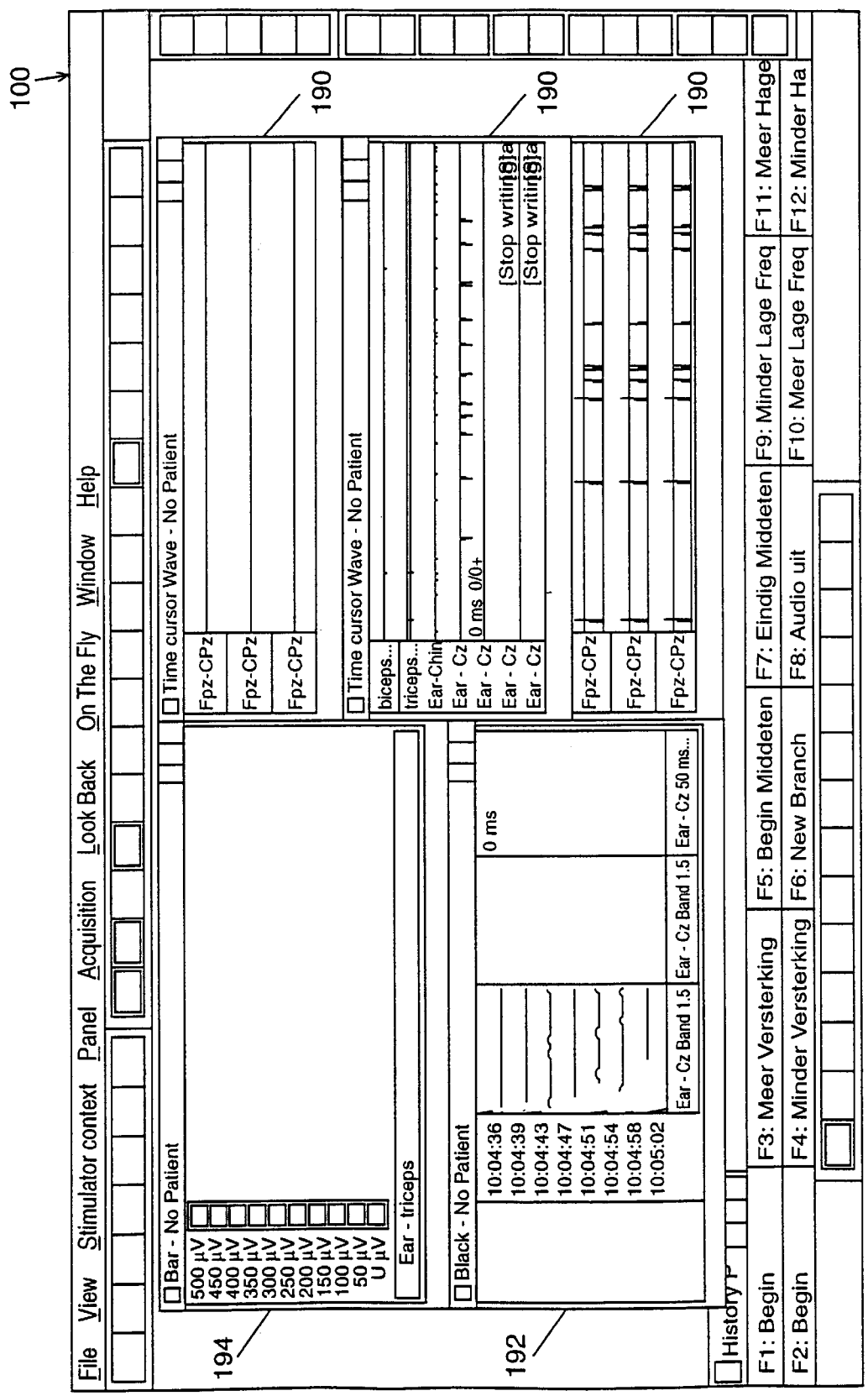

An exemplary operator screen 100 displayed during acquisition mode is shown in FIG. 12. The exemplary screen display shown in FIG. 12 illustrates by example various different panels which have been defined by an operator of the system during the set-up mode to display various signals. The exemplary screen display of FIG. 12 shows exemplary wave panels 190, including a stack panel 192. An exemplary bar indicator panel 194 is also shown. As described previously, the bar indicator panel 194 is used to display parameters associated with a waveform signal. The update rate of the bar indicator panel depends on the type of data being displayed. The data displayed in the bar indicator panel 194 is displayed as a bar with color indicators which may be both size and color coded. For example, a default color scheme for the bar indicator panel 194 may be a heat scale: blue, green, red, yellow, and white. However, an operator of the system 30 is preferably able to define different color scales. The bar indicator panel 194 may preferably be resized, in which case, the indicators in the panel should be resized correspondingly. However, a meaningful lower limit for the indicator size should be enforced. When it the bar indicator panel 194 it is sized to take up the full screen, the bars displayed therein are preferably readable from a distance (e.g., 3 meters on a 14 inch screen). Thus, the bar indicator panel 194 may prove particularly useful in operating room situations or the like.

In accordance with the present invention, the user interface preferably provides for interaction with the various panels defined and the various signals displayed thereon. For example, stack panels 192, and panels showing trend data, allow inspection of the long term environment/context of a measured signal. An operator of the system is preferably able to zoom in and out of such data to review the context of the underlying signal. In a view mode, an operator of the system may employ the user interface pointing device 36 to grab a selected portion of a signal (in a stack panel 192 or trend display) and drag it into a wave panel, to display the corresponding data in a wave panel in a still fashion (the data doesn't scroll). The user interface preferably allows the user to drag a cursor from the stack or trend into an existing panel. This will create a duplicate panel of the type the cursor was dragged into. Signal data corresponding to the cursor position will be displayed accordingly. Of course, such a function may only be available for recorded data, i.e., in preview mode, where data is not recorded, this function cannot be performed.

Figure 13:
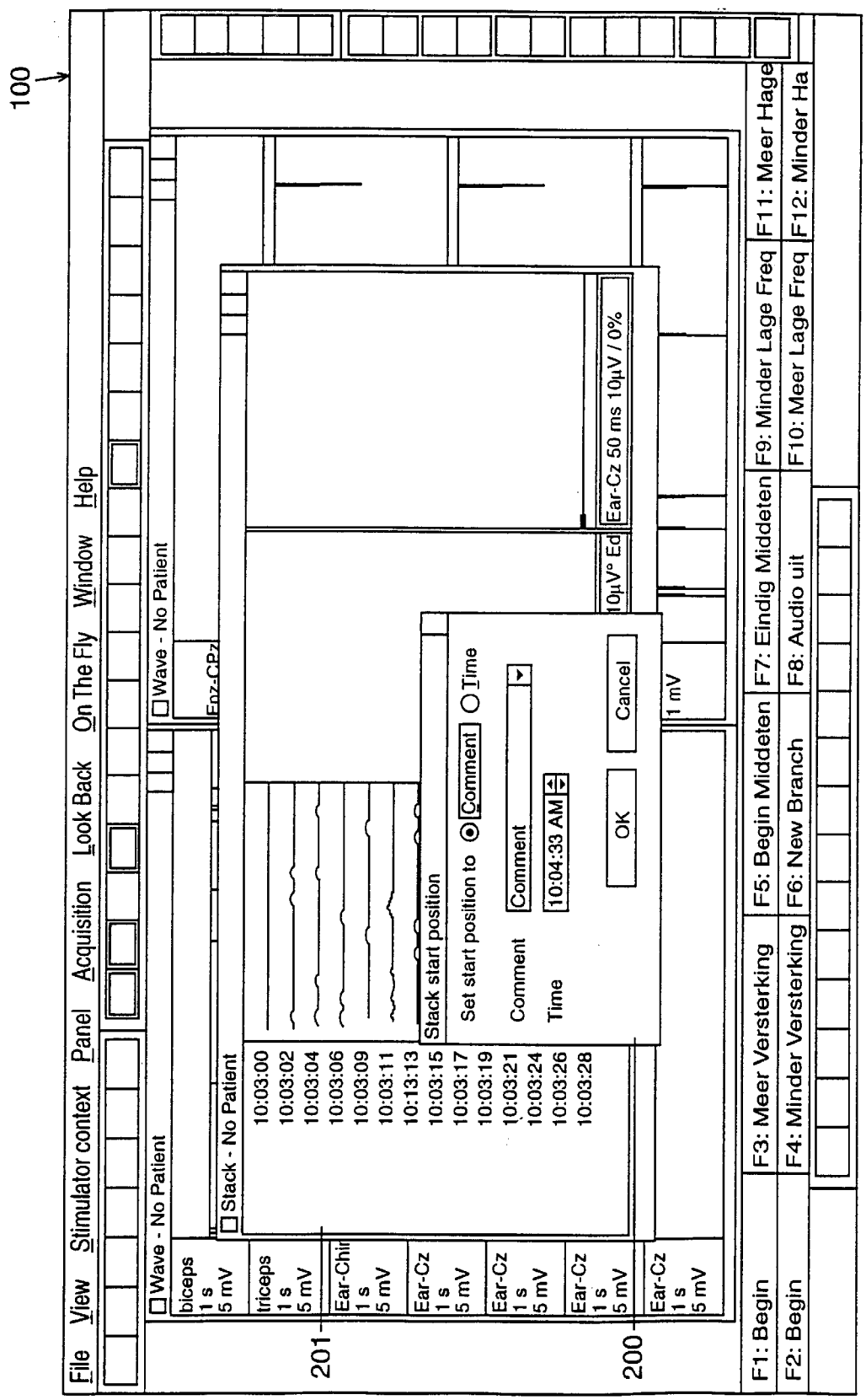

The user interface of a medical monitoring system 30 in accordance with the present invention preferably also provides for the making of remarks, annotations, or comments on the signals displayed in a panel. For example, in a standard wave panel, the user interface preferably provides for the placing of annotations in the signal display area. In a stack panel, a separate column may be made available for textural remarks, annotations, or comments. An exemplary user interface 200 for providing a comment to a stack panel 201 is illustrated in FIG. 13. As illustrated, such comments may be time stamped and/or attached to a specific wave form. Any comments thus made may be compiled in a list that serves as a basis for searching. Such annotations can be made as a fee-text or as a predefined statement. An annotation can be made as a time stamped text or connected to a wave form. The ability to make an annotation synchronized with a video period may also be provided.

Figure 14:
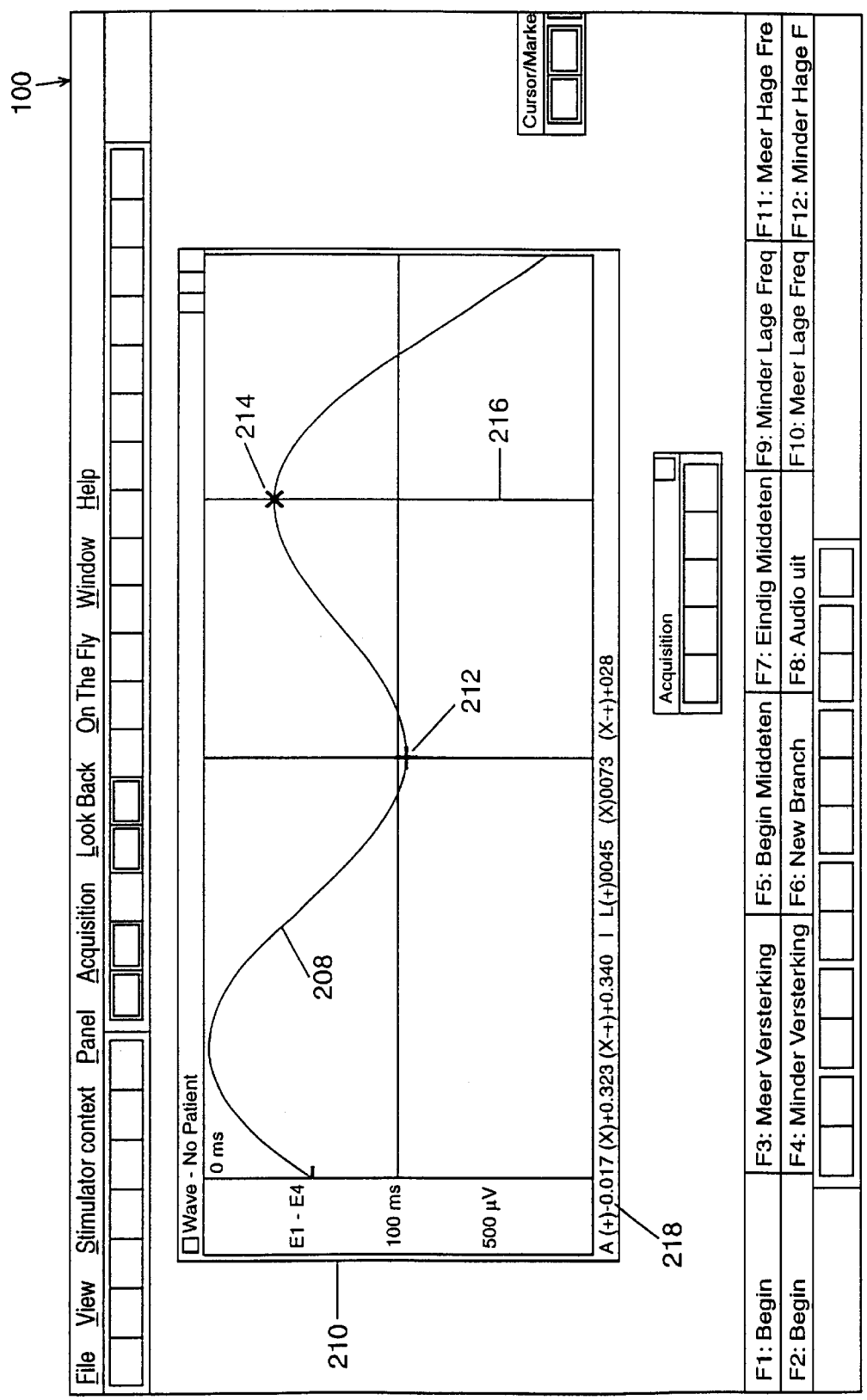

The user interface of a medical monitoring system 30 in accordance with the present invention preferably also provides a tool which allows the operator of the system 30 to measure signal values. For example, a triggered wave form 208 is displayed in a wave panel 210 in FIG. 14. To measure values of the wave form 208 on the fly, two cursors 212 and 214 are provided. One cursor may, for example be in the shape of a "+", the other in the shape of an "X". Other shapes for the cursors 212 and 214 may also be made available, such as bars 216. The two cursors 212 and 214 are placed at desired positions on the wave form 208. A status bar 218 of the panel 210 displays variables associated with the cursor position, for example the amplitude and latencies of both cursors, and the difference of the amplitude and latency values. Thus, the cursors 212 and 214 provide a ruler that allows a quick measurement of a wave form 208.

Figure 15:
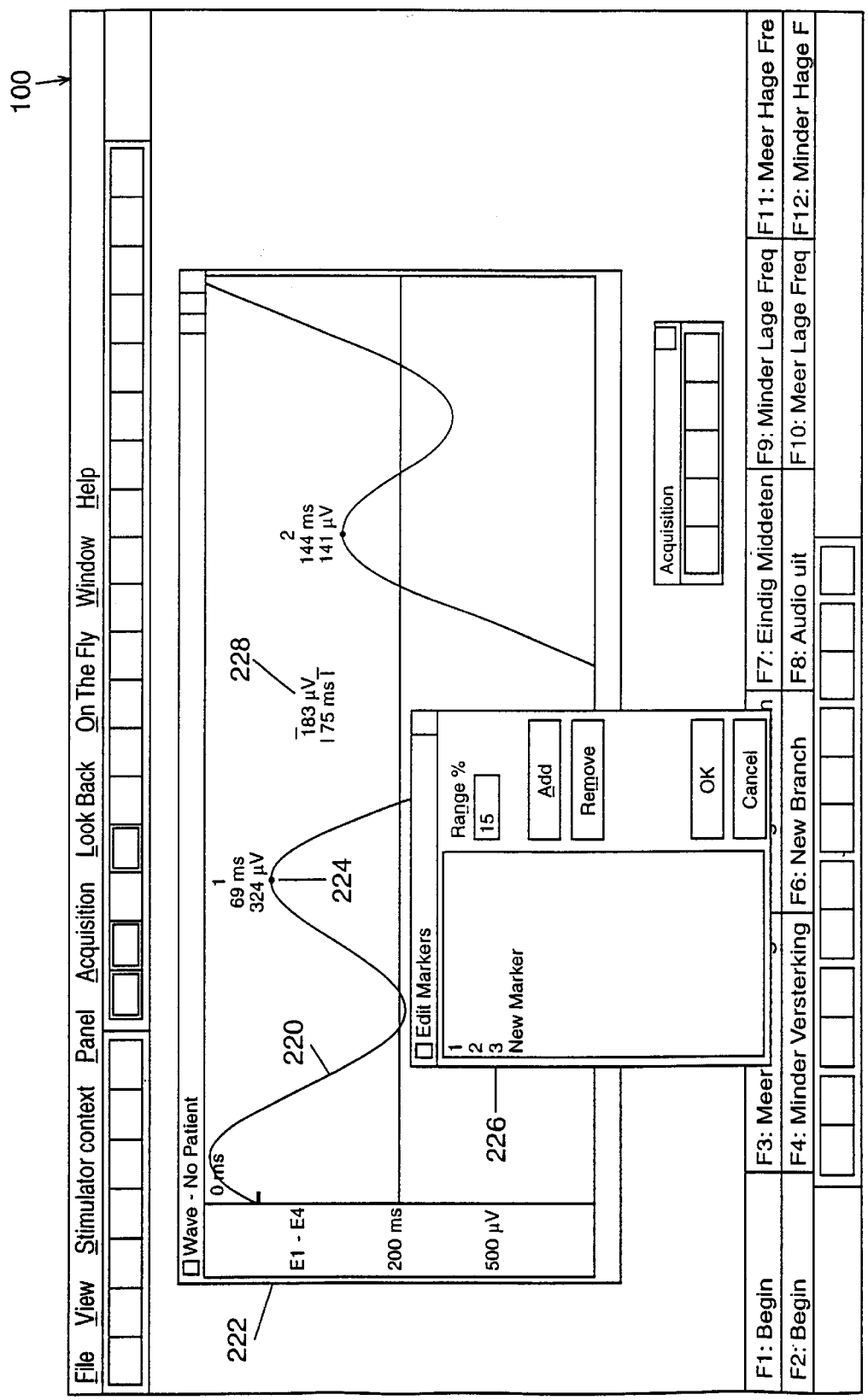

Another user interface method which is preferably provided to measure values of a wave form employs markers. The use of markers in accordance with the present invention is described, for example, with reference to FIG. 15, where a wave form 220 displayed in a wave panel 222 is to be measured. The use of markers to measure a wave form may be performed on either triggered or averaged data. An operator may preferably turn on a plurality, e.g., up to 7, markers per wave form. Markers can detect and mark peaks or valleys. The first time a wave is measured, markers 224 are set by an operator of the system 30, e.g., using the mouse 36. When a marker 224 is placed, the system 30 automatically sets the marker until the operator redefines the marker by overriding the system position. When a marker is set, the software recognizes if it is a peak or trough (maximum or a minimum). The system looks for the same peak or trough within X% of the latency of the defined one in all subsequent wave forms. The value of the percentage can be defined by an operator, e.g., via user interface window 226, as illustrated, for example, in FIG. 15. The label, latency, and/or amplitude (absolute and relative) of the detected extreme values in the wave form 220 can thus be displayed 228 using the markers 224. As illustrated in FIG. 15, displayed relative amplitude or latency 228 is relative to the following marker in sequence. The values of marked waves may also be stored in a measurement table, as they come in with a time stamp. Those values may be displayed or exported to a report generator or spreadsheet for further analysis.

Figure 16:
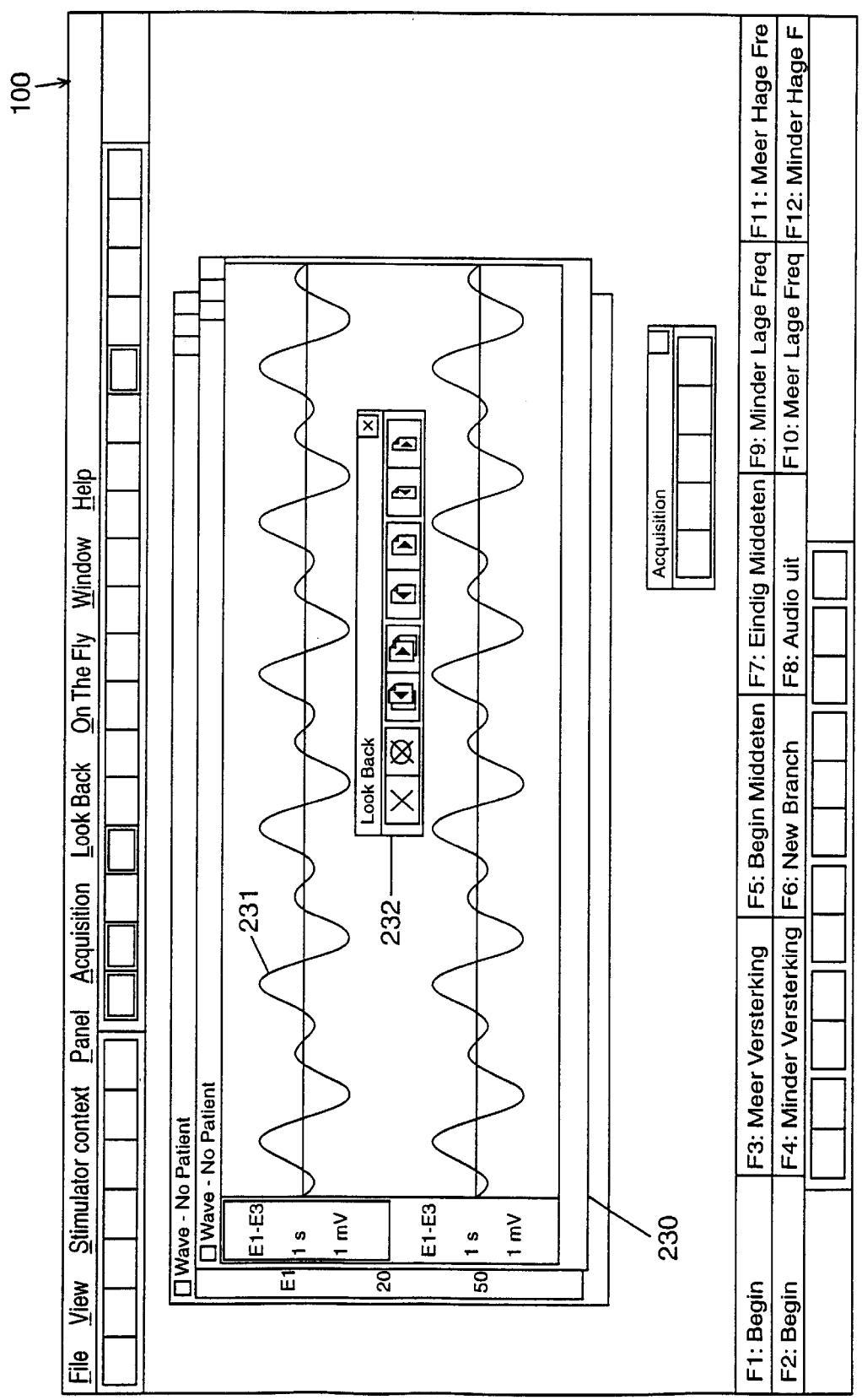

A user interface for a medical signal monitoring system 30 in accordance with the present invention preferably provides a look-back mode, enabling an operator of the system 30 to examine more carefully a portion of a wave form passing through a wave panel. An exemplary look-back window 230 is illustrated in FIG. 16. The look-back window shows a segment 231 of a previously recorded (and displayed) wave form. For example, up to ten seconds of the wave form 231 may be shown in the look-back window. The wave form 231 shown in the look-back window 230 is frozen in time. A look-back control panel 232 is provided, whereby an operator of the system can scroll backward or forward in time, thereby changing the portion of the wave form 231 shown in the look-back window 230, to find and observe in more detail a particular portion of the wave form of interest. When the look-back mode is terminated, the wave form 231 is released from its frozen state, and is resynchronized with active acquisition, i.e., the wave form displayed jumps forward to real-time.

As mentioned previously, a medical signal monitoring system 30 in accordance with the present invention may preferably be used to control a stimulator system 50 for providing stimulation signals to a subject 46. The user interface of a monitoring system 30 in accordance with the present invention preferably provides a mechanism for defining the stimulation to be applied to the subject 46, as well as for coordinating the display of response signals received by the system 30 from the subject 46 in response to the stimulation provided. For example, as discussed previously, signals to be displayed by the monitoring system 30 may be triggered based upon stimulus signals. Similarly, an averaged signal to be displayed may be averaged based on the occurrence of a stimulus signal.

Preferably, the user interface allows a set of stimulus settings to be established for each panel of signals to be displayed. The stimulus settings for a signal panel is defined as a stimulus context. Different panels may have different stimulus contexts. One set of stimulus settings may be defined as the stimulus context for one panel, with another set of stimulus settings established as the stimulus context for another panel. The stimulus that is actually provided to a subject is determined by selecting one of the panels, and, therefore, the stimulus context of that panel, as the active panel. The stimulation to be provided to a subject may be changed easily during acquisition, by simply selecting a different panel, and, therefore, a different stimulus context, as the active panel. A more detailed discussion of the concept of establishing a stimulus context will now be provided.

Figure 17:
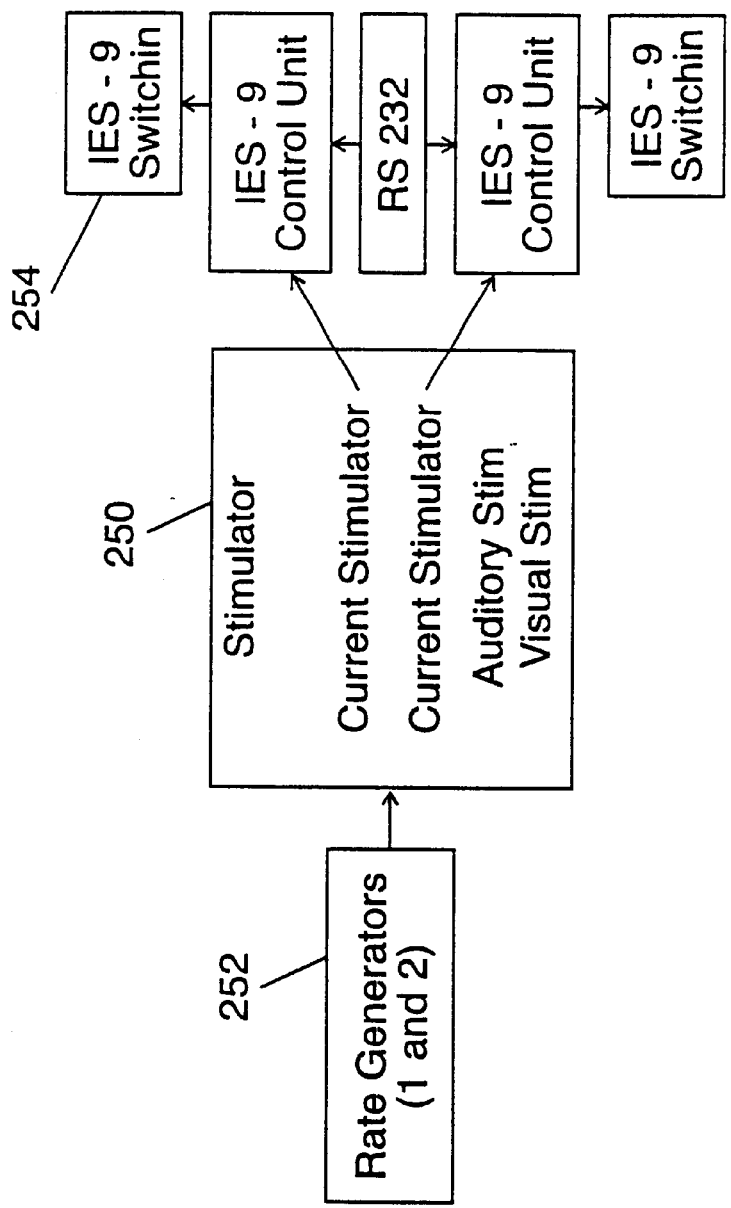
FIG. 17 is a schematic block diagram of available stimulus generators and stimulus modalities for an exemplary medical signal monitoring system in accordance with the present invention.

An exemplary method of stimulus generation will be described with reference to the schematic block diagram of FIG. 17. As described previously, a medical signal monitoring system 30 in accordance with the present invention may be used to drive various stimulator devices 250. Such stimulator devices may include, one or more electrical (current) stimulators, an auditory stimulator, and/or a visual stimulator. The various stimulators 250 are driven by one or more rate generators 252 implemented in the monitoring system computer 32. Preferably a plurality of rate generators are available, with each rate generator connected via switching mechanisms to one or more of the available stimulator devices 250. The different rate generators may each be synchronized with averaged or triggered signal acquisition, in order to allow pseudo simultaneous data acquisition. In the example of FIG. 17, two triggers or rate generators are provided to be connected to various stimulators 250. Both generators 252 can be connected any of the stimulators 250 using conventional software controled switches. The electrical stimulators 250 may be multiplexed, via stimulus switching devices 254, in the stimulator system 50.

Figure 18:
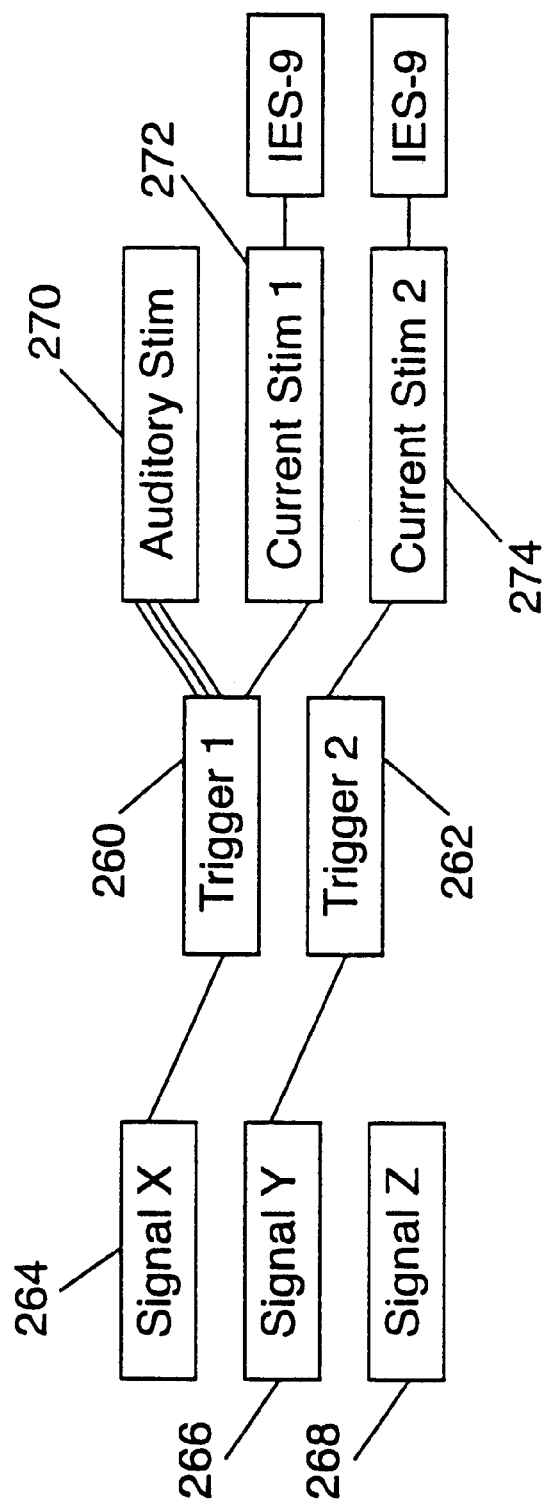
FIG. 18 is a schematic block diagram of an exemplary stimulator context established using the user interface of a medical monitoring system in accordance with the present invention.

An example of a stimulus setting, based on the diagram of stimulus generation presented in FIG. 17, which may be established using the user interface of the present invention, is illustrated in FIG. 18. Two rate generators (triggers) 260 and 262 are employed. Three traces or signals to be displayed are defined by an operator of the system 30 employing the user interface in the manner described above. One of the signals to be displayed, signal Z 268, is defined as a free-run signal. Thus, the display of signal Z in a panel is not tied to any stimulation signal. The other two traces, signal X 264 and signal Y 266, are synchronized to different triggers 260 and 262, respectively. The first rate generator (trigger 1) 260 is, in turn, coupled to provide trigger signals to an auditory stimulator 270 and an electrical current stimulator 272. Thus, signal X to be displayed is synchronized to auditory and electrical current stimulation signals. The second rate generator (trigger 2) 262 is connected to control a second current stimulator 274. Thus, the display of signal Y is synchronized to stimulus signals provided to a subject 46 via electrical current stimulator 274. The auditory stimulator device 270 generates clicks, the electrical current stimulator devices 270 and 274 generate current pulses, and, if available, a visual stimulator would provide light flashes, at the occurrence of triggers provided by the rate generator trigger devices 260 and 262. A measured signal is synchronized with the stimuli. Thus, in the example of FIG. 18, displayed signal X is synchronized with trigger 1 and displayed signal Y with trigger 2. This results in a panel wherein each signal trace X and Y is the result of a different stimulator. However, they are recorded in the same time interval. The multiplexing of the stimulators may be accomplished by switching the periodically in a round-robin fashion.

FIG. 18 illustrates a stimulus context for one panel. Other stimulus contexts may be defined for other panels. The context of the stimulation provided to a subject is changed by selecting different panels in the user interface.

Figure 19:
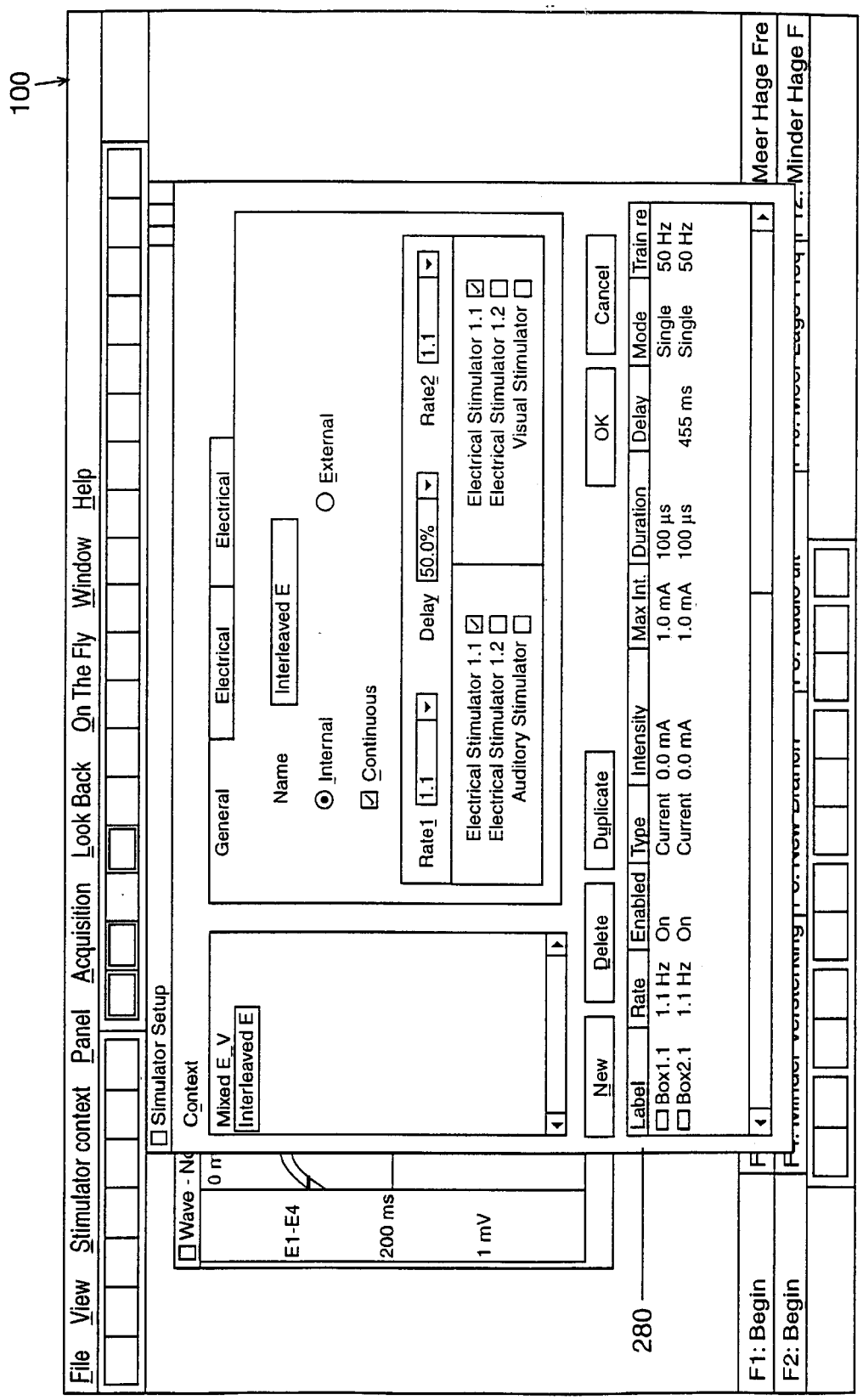

An exemplary user interface for establishing a stimulus context is illustrated at 280 in FIG. 19. The stimulator set-up user interface 280 allows an operator of the system 30 to define the rate, duration of stimulus, etc., of the stimulators, as well as to define the stimulators that are on. It also allows the operator to specify the pattern in which the electrical stimulators, visual stimulator and auditory stimulator are activated. An operator defines the pattern itself in the context set-up. In the panel set-up described previously, the operator selects a context, from a list of thus defined contexts, for a panel, if desired. Because the context is global for a panel, switching from one context to another is done by switching the active panel. Each signal in the panel can be synchronized with a unique stimulator channel. The stimulator set-up user interface 280 is used to define a stimulator context by entering a name for the context, and determining how to control the stimuli. Control may be either internal or external. In the case of internal control, the stimuli are continuous or gated. Either one or both of the two available rate generators, in this case, are selected to be attached to the stimulators, which may be, as discussed above, electrical, auditory, or visual. Rates and the delay between the two generators can be set. Additional user interface windows allow other settings to be established by the operator, such as, for example, duration, type, maximum intensity, intensity, stimulus site, mode, train rate, etc., for electrical stimulators, duration, polarity, transducer, and decibels, for each of left and right auditory stimulators, and mode, train rate, and count for visual stimulators, etc. Once a stimulator context has been established, it may be selected during panel set-up, to thereby assign the particular stimulator context to a particular panel of signals to be displayed.

Figure 20:
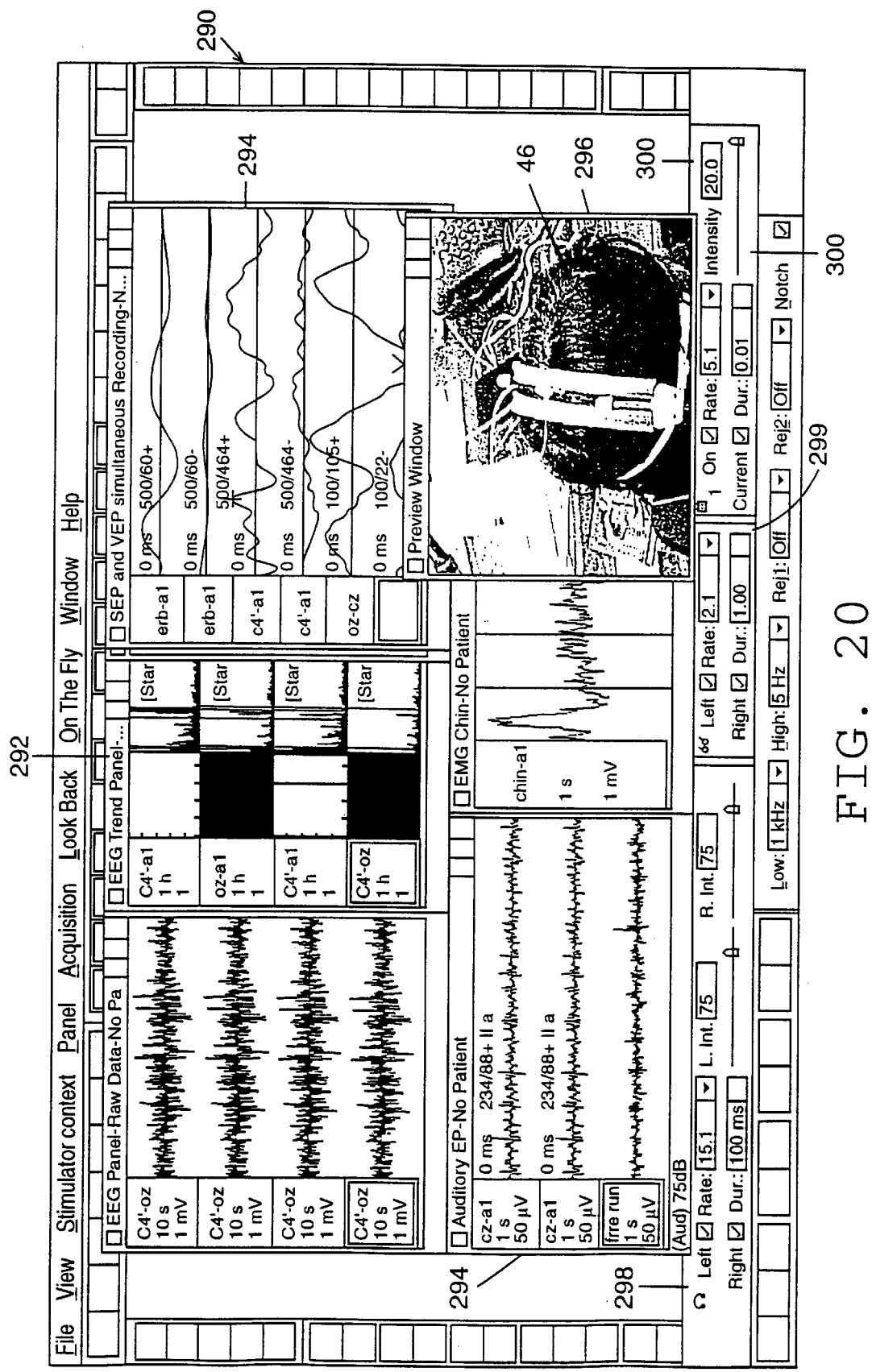

An exemplary screen display provided by a medical signal monitoring system 30 in accordance with the present invention is illustrated at 290 in FIG. 20. Exemplary screen display 290 includes various panels as defined during set-up mode, displaying various different types of data. These panels include a trend panel 292, as well as panels 294 showing evoked potential wave forms in response to stimulus signals, wherein the stimulator context is defined for each panel in the manner described previously. The screen display 290 of FIG. 20 also shows, for example, a video window 296 in which, for example, a video image of a subject 46 taken by the video camera 52 may be displayed. Also shown are user interfaces 298, 299, and 300 for controlling, in real-time, various parameters of auditory, visual, and electrical stimulation, respectively, being applied to the subject 46.

It should be understood that many of the signal processing functions mentioned herein may be performed in a conventional manner. A medical signal monitoring system 30 in accordance with the present invention may be coupled to other software programs, such as patient databases, report generators (word processors), and/or spreadsheets, to exchange data therebetween in a conventional manner.

It is understood that the present invention is not limited to the particular embodiments, examples, and applications illustrated and described herein, but embraces all such modified forms thereof as, as come within the scope of the following claims.

What is claimed is:

1. A medical monitoring system for displaying physiological signals from a subject, comprising:
    (a) a computer system for receiving physiological signals from a subject via an acquisition system and including means for recording the physiological signals from the subject, means for receiving operator commands, and a computer display for displaying signals to an operator of the system; and
    (b) a user interface implemented in the computer system, displayed on the means for displaying signals to an operator of the system, accessed by an operator of the system via the means for receiving operator commands, and including means for selecting a panel in which a physiological signal is to be displayed from a plurality of available panel types for defining the format of the signal to be displayed, wherein a different format for displaying a physiological signal is assigned to each panel type, and means for defining the signal to be displayed in the panel, and the modality of the signal to be displayed.

2. The medical monitoring system of claim 1 wherein the means for recording the physiological signals includes a disk memory storage system.

3. The medical monitoring system of claim 1 where the means for receiving operator commands is selected from the group of computer system input devices consisting of a keyboard and a mouse.

4. The medical monitoring system of claim 1 wherein a format for displaying a physiological signal assigned to a one of the panel types includes a wave format for displaying the physiological signal as a waveform.

5. The medical monitoring system of claim 4 wherein the formats for displaying physiological signals assigned to the panel types include a standard wave format for displaying the physiological signal as a waveform scrolling from right to left, a sweep line wave format for displaying the physiological signal as a waveform scrolling from left to right, and a stack panel wave format for displaying the physiological signal as waveforms in a column scrolling in a vertical direction.

6. The medical monitoring system of claim 4 wherein the formats for displaying physiological signals assigned to the panel types includes additionally an indicator panel format for displaying a characteristic of the physiological signal as an area of a bar.

7. The medical monitoring system of claim 1 wherein the physiological signals received by the computer system are electrical physiological signals received from a plurality of electrodes attached to the subject.

8. The medical monitoring system of claim 7 wherein the means for defining the signal to be displayed in a panel includes means for selecting signals provided by a pair of the plurality of electrodes attached to the subject, and wherein the computer system includes means for deriving a montaged signal from the selected signals.

9. The medical monitoring system of claim 8 wherein the means for defining the modality of the signal to be displayed includes means for selecting the modality of the signal to be displayed from a plurality of modalities including EEG and EMG.

10. The medical monitoring system of claim 9 wherein the means for defining the modality of the signal to be displayed includes means for selecting the modality of the signal to be displayed from a plurality of modalities including evoked potentials.

11. A method for displaying physiological signals of a subject, comprising the steps of:
    (a) providing a plurality of electrical physiological signals from a plurality of electrodes attached to a subject;
    (b) selecting a panel in which a physiological signal is to be displayed from a plurality of panel types, wherein a different format for displaying a physiological signal is assigned to each panel type;
    (c) defining a signal to be displayed by selecting a pair of electrical physiological signals from the plurality of electrical physiological signals and deriving a montaged pair signal to be displayed from the pair of electrical physiological signals selected;
    (d) selecting a modality of the physiological signal to be displayed; and
    (e) displaying the montaged pair physiological signal in the panel in the format assigned and the modality selected.

12. The method of claim 11 comprising the additional steps of:
    defining a stimulation context defining stimulation to be applied to the subject, assigning the stimulation context to the selected panel, and controlling the providing of stimulation to the subject in the manner defined by the stimulation context when the panel is activated.

13. The method of claim 12 wherein the signal displayed in the panel is a triggered signal which is triggered by the stimulation applied to the subject.

14. A method for controlling stimulation applied to a subject and displaying physiological signals of the subject in response thereto, comprising the steps of:
    (a) providing a plurality of physiological signals from a subject;
    (b) selecting a panel in which a physiological signal is to be displayed;
    (c) selecting at least one signal derived from the plurality of signals to be displayed in the panel;
    (d) defining a stimulation context defining the stimulation to be applied to the subject;
    (e) assigning the stimulation context to the selected panel; and
    (f) controlling the providing of stimulation to the subject in the manner defined by the stimulation context and displaying the physiological signal in the panel when the panel is activated.

15. The method of claim 14 wherein the plurality of physiological signals received from the subject are electrical physiological signals received from a plurality of electrodes attached to the subject.

16. The method of claim 15 wherein the step of selecting at least one signal derived from the plurality of signals to be displayed in the panel includes the step of selecting a pair of electrical physiological signals from the plurality of electrical physiologic signals and deriving a montaged pair signal to be displayed from the pair of electrical physiological signals selected.

17. The method of claim 14 wherein the step of selecting a panel in which the physiological signal is to be displayed includes the step of selecting a panel from a plurality of panel types wherein a different format for displaying a physiological signal is assigned to each panel type.

18. The method of claim 14 wherein the physiological signal displayed in the panel is a triggered signal which is triggered by the stimulation applied to the subject.

19. A medical monitoring system for controlling the providing of stimulation to a subject and for displaying physiological signals of the subject in response thereto, comprising:
   (a) a computer implemented system for controlling a stimulation system for providing stimulation signals to the subject, for receiving a plurality of physiological signals from the subject, and for displaying the physiological signals received from the subject;
   (b) means for selecting panels in which the physiological signals from the subject will be displayed and for selecting at least one signal derived from the plurality of physiological signals to be displayed in each panel;
   (c) means for assigning a stimulation context defining the stimulation to be applied to the subject to each panel; and
   (d) means for controlling the stimulation system to provide stimulation to the subject in the manner defined by a stimulation context in response activation of a panel having the stimulation context assigned thereto.

20. The medical monitoring system of claim 19 comprising additionally a stimulation system connected to and controlled by the medical monitoring system for providing stimulation signals to the subject, wherein the stimulation system includes one or more stimulators selected from the group of stimulators consisting of electrical stimulators, audio stimulators, and visual stimulators.

21. The medical monitoring system of claim 19 comprising additionally a physiological signal acquisition system for providing the plurality of physiological signals from the subject to the medical monitoring system, wherein the physiological signal acquisition system includes a plurality of electrodes attached to the subject to detect electrical physiological signals from the subject.

22. The medical monitoring system of claim 19 wherein the signal to be displayed in the panel is a triggered signal the display of which is triggered in response to the stimulation provided to the subject.

23. A method for displaying physiological signals of a subject, comprising the steps of:
   (a) receiving a plurality of raw wide band physiological signals from a plurality of portions of a subject's body;
   (b) selecting at least one first pair of the plurality of raw wide band physiological signals;
   (c) selecting a first modality of interest;
   (d) combining and filtering the first pair of raw wide band physiological signals for the modality of interest to define a first physiological signal to be displayed; and
   (e) displaying the first physiological signal to be displayed.

24. The method of claim 23 wherein the step of receiving a plurality of raw wide band physiological signals includes the step of attaching a plurality of electrodes to the plurality of portions of the subject's body.

25. The method of claim 23 wherein the step of receiving a plurality of raw wide band physiological signals includes the step of receiving a plurality of electrical physiological signals wherein a frequency range of each electrical physiological signal is wide enough to include EEG, EMG and EP frequency bands.

26. The method of claim 25 wherein the step of selecting a first modality of interest includes the step of selecting a frequency range corresponding to a frequency band selected from the group of frequency bands consisting of EEG, EMG and EP frequency bands.

27. The method of claim 23 wherein the step of combining the first pair of raw wide band physiological signals includes the step of montaging the first pair of raw wide band physiological signals.

28. The method of claim 23 comprising additionally the step of defining a format in which the first physiological signal to be displayed is displayed.

29. The method of claim 28 wherein the step of defining a format in which the first physiological signal to be displayed is displayed includes the step of selecting a panel in which the first physiological signal to be displayed is to be displayed from a plurality of panel types, wherein a different format for displaying a physiological signal is assigned to each panel type.

30. The method of claim 23 comprising additionally the steps of:
   (a) selecting a second pair of the plurality of raw wide band physiological signals;
   (b) selecting a second modality of interest;
   (c) combining and filtering the second pair of raw wide band physiological signals for the second modality of interest to define a second physiological signal to be displayed; and
   (d) displaying the second physiological signal to be displayed.

31. The method of claim 30 wherein the second pair of raw wide band physiological signals includes at least one raw wide band physiological signal included in the first pair of raw wide band physiological signals.

32. The method of claim 31 wherein the second modality of interest is different from the first modality of interest.

33. The method of claim 30 wherein the second physiological signal to be displayed is displayed simultaneously with the first physiological signal to be displayed.

34. The method of claim 23 comprising additionally the step of saving the plurality of raw wide band physiological signals.

35. The method of claim 34 comprising additionally the steps of:
   (a) selecting at least one pair of the saved plurality of raw wide band physiological signals;
   (b) selecting a third modality of interest;
   (c) combining and filtering the selected pair of saved raw wide band physiological signals for the third modality of interest to define a third physiological signal to be displayed; and (d) displaying the third physiological signal to be displayed.

36. The method of claim 35 wherein the selected pair of saved raw wide band physiological signals includes at least one raw wide band physiological signal corresponding to at least one of the raw wide band physiological signals included in the first pair of raw wide band physiological signals.

37. The method of claim 35 wherein the third modality of interest is different from the first modality of interest.

38. A medical monitoring system for displaying physiological signals of a subject, comprising:
   (a) means for receiving a plurality of raw wide band physiological signals from a plurality of portions of a subject's body;
   (b) a user interface for selecting pairs of the plurality of raw wide band physiological signals, wherein any one of the raw wide band physiological signals may be included in more than one pair, and for selecting a modality for each selected pair of raw wide band physiological signals;
   (c) means for combining and filtering the signals in each selected pair of raw wide band physiological signals for the corresponding modality to define physiological signals to be displayed; and
   (d) means for displaying the physiological signals to be displayed.

39. The medical monitoring system of claim 38 wherein the means for receiving a plurality of raw wide band physiological signals includes a physiological signal acquisition system including a plurality of electrodes attached to the plurality of portions of the subject's body.

40. The medical monitoring system of claim 39 wherein the physiological signal acquisition system provides a plurality of electrical physiological signals wherein a frequency range of each electrical physiological signal is wide enough to include EEG, EMG and EP frequency bands.

41. The medical monitoring system of claim 38 wherein the user interface for selecting a modality for each selected pair of raw wide band physiological signals includes means for selecting a frequency range corresponding to a frequency band selected from the group of frequency bands consisting of EEG, EMG and EP frequency bands for each selected pair of raw wide band physiological signals.

42. The medical monitoring system of claim 38 wherein the means for combining the signals in each selected pair of raw wide band physiological signals includes means for montaging the signals in each selected pair of raw wide band physiological signals.

43. The medical monitoring system of claim 38 comprising additionally means for defining formats in which the physiological signals to be displayed are displayed.

44. The medical monitoring system of claim 43 wherein the means for defining formats in which the physiological signals to be displayed are displayed includes means for selecting panels in which the physiological signals to be displayed are to be displayed from a plurality of panel types, wherein a different format for displaying a physiological signal is assigned to each panel type.

45. The medical monitoring system of claim 38 comprising additionally means for saving the plurality of raw wide band physiological signals.

46. The medical monitoring system of claim 45, wherein the user interface includes means for selecting pairs of the saved plurality of raw wide band physiological signals, wherein any one of the saved plurality of raw wide band physiological signals may be included in more than one pair, and for selecting a modality for each selected pair of saved raw wide band physiological signals; wherein the means for combing and filtering includes means for combining and filtering the selected pairs of saved raw wide band physiological signals for the corresponding modality to define physiological signals to be displayed; and wherein the means for displaying includes means for displaying the physiological signals to be displayed.

* * * * *